US010061064B2

United States Patent
Umetsu et al.

(10) Patent No.: US 10,061,064 B2
(45) Date of Patent: *Aug. 28, 2018

(54) PRISM AND SENSOR CHIP

(71) Applicant: Konica Minolta, Inc., Chiyoda-ku, Tokyo (JP)

(72) Inventors: Hiroshi Umetsu, Tachikawa (JP); Yoshihiro Okumura, Toyohashi (JP); Takehiko Goshima, Kunitachi (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/189,515

(22) Filed: Jun. 22, 2016

(65) Prior Publication Data

US 2016/0299266 A1 Oct. 13, 2016

Related U.S. Application Data

(63) Continuation of application No. 14/387,864, filed as application No. PCT/JP2013/058400 on Mar. 22, 2013, now Pat. No. 9,435,919.

(30) Foreign Application Priority Data

Mar. 26, 2012 (JP) .................. 2012-070390

(51) Int. Cl.
*G01J 1/58* (2006.01)
*G02B 5/04* (2006.01)
(Continued)

(52) U.S. Cl.
CPC ............. *G02B 5/04* (2013.01); *G01N 21/648* (2013.01); *G02B 1/04* (2013.01); *G02B 5/008* (2013.01)

(58) Field of Classification Search
CPC .... G01N 21/05; G01N 21/648; G02B 6/1226; G02B 5/008; G02B 5/04; G02B 1/04
(Continued)

(56) References Cited

U.S. PATENT DOCUMENTS 6,049,429 A * 4/2000 Iizuka ...................... G02B 5/04
                                                        359/631
6,165,407 A * 12/2000 Tahara .................... B29C 45/37
                                                        249/111
(Continued)

FOREIGN PATENT DOCUMENTS

CN          101952710          1/2011
JP          05085752 A         4/1993
(Continued)

OTHER PUBLICATIONS

Chinese First Examination Opinion Notice corresponding to Patent Application No. 201380016537.0; dated Mar. 2, 2016, with English translation.
(Continued)

*Primary Examiner* — Taeho Jo
(74) *Attorney, Agent, or Firm* — Cantor Colburn LLP

(57) ABSTRACT

A prism used in analysis utilizing surface plasmons is prism of a dielectric medium with a predetermined reflective index. Trapezoidal prism comprises an incident surface on which excitation light is incident from outside, a reflective surface at which the excitation light incident on the incident surface is reflected, an emission surface from which the excitation light reflected by the reflective surface is emitted; and an opposite surface which opposes the reflective surface. The opposite surface is a recessed sink mark surface.

12 Claims, 24 Drawing Sheets

(51) Int. Cl.
  *G01N 21/64* (2006.01)
  *G02B 5/00* (2006.01)
  *G02B 1/04* (2006.01)

(58) Field of Classification Search
  USPC .................................................. 250/458.1
  See application file for complete search history.

(56) References Cited

U.S. PATENT DOCUMENTS

| | | | | |
|---|---|---|---|---|
| 6,297,907 | B1* | 10/2001 | Wang | G02B 27/288 349/106 |
| 6,340,448 | B1* | 1/2002 | Naya | G01N 21/553 356/445 |
| 6,704,052 | B1* | 3/2004 | Togino | G02B 5/04 348/335 |
| 6,707,622 | B2* | 3/2004 | Tominaga | B29C 45/0025 264/1.1 |
| 7,330,263 | B2* | 2/2008 | Ohtsuka | B82Y 15/00 356/246 |
| 8,106,368 | B2* | 1/2012 | Ohtsuka | G01N 21/6428 250/458.1 |
| 8,193,516 | B2* | 6/2012 | Kimura | G01N 21/648 250/458.1 |
| 8,372,476 | B2* | 2/2013 | Katsuhara | B82Y 20/00 356/301 |
| 2002/0030900 | A1* | 3/2002 | Tominaga | B29C 45/0025 359/831 |
| 2002/0030901 | A1* | 3/2002 | Kobayashi | G02B 5/04 359/831 |
| 2002/0127706 | A1* | 9/2002 | Naya | G01N 21/553 435/287.2 |
| 2003/0048453 | A1* | 3/2003 | Mori | G01N 21/0332 356/445 |
| 2003/0062842 | A1* | 4/2003 | Nomura | G01N 21/553 315/149 |
| 2003/0099422 | A1* | 5/2003 | Beom | B82Y 20/00 385/12 |
| 2003/0184755 | A1* | 10/2003 | Mori | G01N 21/553 356/445 |
| 2003/0219809 | A1* | 11/2003 | Chen | G01N 21/553 506/4 |
| 2004/0130723 | A1* | 7/2004 | Yager | G01N 21/553 356/445 |
| 2005/0018007 | A1* | 1/2005 | Ujita | B41J 2/17566 347/19 |
| 2005/0110989 | A1* | 5/2005 | Schermer | G01N 21/253 356/246 |
| 2005/0168746 | A1* | 8/2005 | Ohtsuka | B82Y 15/00 356/445 |
| 2005/0229696 | A1* | 10/2005 | Takayama | B01F 5/0646 73/204.26 |
| 2006/0082779 | A1* | 4/2006 | Muraishi | B01L 3/502 356/445 |
| 2006/0170927 | A1* | 8/2006 | Wang | G01N 21/553 356/445 |
| 2007/0244241 | A1* | 10/2007 | Masuda | C08K 9/04 524/436 |
| 2007/0291262 | A1* | 12/2007 | Candiloro | G01N 21/253 356/244 |
| 2008/0174774 | A1* | 7/2008 | Bratkovski | G01N 21/658 356/301 |
| 2009/0218499 | A1* | 9/2009 | Kimura | G01N 21/47 250/363.01 |
| 2009/0275016 | A1* | 11/2009 | Miller | G01N 21/05 435/5 |
| 2009/0283700 | A1* | 11/2009 | Ohtsuka | G01N 21/6428 250/459.1 |
| 2010/0014546 | A1* | 1/2010 | Matsumoto | B82Y 20/00 372/25 |
| 2010/0075300 | A1* | 3/2010 | Miller | G01N 33/54373 435/5 |
| 2010/0091266 | A1 | 4/2010 | Yasuda et al. | |
| 2010/0092792 | A1* | 4/2010 | Inari | B32B 15/08 428/458 |
| 2010/0128273 | A1* | 5/2010 | Lee | G01N 21/553 356/445 |
| 2010/0128274 | A1* | 5/2010 | Kimura | G01N 21/553 356/445 |
| 2010/0195107 | A1* | 8/2010 | Naya | G01N 21/553 356/445 |
| 2010/0252751 | A1* | 10/2010 | Klunder | B82Y 15/00 250/459.1 |
| 2011/0157593 | A1* | 6/2011 | Miyadera | G01N 21/553 356/445 |
| 2011/0267621 | A1* | 11/2011 | Nakatani | G01N 21/554 356/445 |
| 2011/0310383 | A1* | 12/2011 | Masson | G01N 21/553 356/319 |
| 2012/0028247 | A1* | 2/2012 | Tamura | G01N 21/553 435/5 |
| 2012/0154814 | A1* | 6/2012 | Zare | G01N 21/553 356/445 |
| 2012/0156800 | A1* | 6/2012 | Aoki | G01N 21/553 436/180 |
| 2012/0201716 | A1* | 8/2012 | Matsuo | G01N 21/553 422/69 |
| 2013/0078146 | A1* | 3/2013 | Sando | G01N 21/648 422/69 |

FOREIGN PATENT DOCUMENTS

| | | | |
|---|---|---|---|
| JP | 07069651 A | | 3/1995 |
| JP | 08234005 A | * | 9/1996 |
| JP | H108234005 A | | 9/1996 |
| JP | 08294945 A | * | 11/1996 |
| JP | 2003106992 A | | 4/2003 |
| JP | 2003240705 A | | 8/2003 |
| JP | 2006187972 A | | 7/2006 |
| JP | 2008224449 A | | 9/2008 |
| JP | 2009236709 A | | 10/2009 |

OTHER PUBLICATIONS

International Search Report for International Application No. PCT/JP2013/058400; dated May 28, 2013; with English translation.
U.S. Non Final Office Action corresponding to U.S. Appl. No. 14/387,864; dated Nov. 5, 2015.

* cited by examiner

FIG. 20

| | COMPARISON | EXAMPLE 1 | EXAMPLE 2 | EXAMPLE 3 |
|---|---|---|---|---|
| | 2-POINT EJECTION WITH EJECTION MECHANISM ON GATE EXTENSION REGION | 2-POINT EJECTION WITH EJECTION MECHANISM ON GATE EXTENSION REGION | CORE EJECTION WITH EJECTION MECHANISM ON GATE EXTENSION REGION | 4-POINT EJECTION WITHOUT EJECTION MECHANISM ON GATE EXTENSION REGION AND WITHIN RAY INCIDENT RANGE |
| SINK-MARK ON THE SINK-MARK SURFACE | WITHOUT SINK MARK (sink-mark amount (height) 3 μm OR LESS) | WITHOUT SINK MARK (sink-mark amount (height) 2 5 μm OR MORE) | WITHOUT SINK MARK (sink-mark amount (height) 25 μm OR MORE) | WITHOUT SINK MARK (sink-mark amount (height) 25 μm OR MORE) |
| P-DEFLECTION MAINTENANCE RATE AND DISTRIBUTION THEREOF | ✕ | ◯ | ◯ | ◎ |

US 10,061,064 B2

PRISM AND SENSOR CHIP

CROSS REFERENCE TO RELATED APPLICATIONS

This application is a continuation application of U.S. patent application Ser. No. 14/387,864, filed on Sep. 25, 2014, which is the U.S. national stage of application No. PCT/JP2013/058400, filed on Mar. 22, 2013, which claims priority under 35 U.S.C. § 119(a) and 35 U.S.C. § 365(b) to Japanese patent Application No. 2012-070390, filed Mar. 26, 2012, the disclosures of which are incorporated herein by reference in their entirety.

TECHNICAL FIELD

The present invention relates prisms and sensor chips used for measuring apparatuses for performing measurement utilizing surface plasmons and measurement utilizing the surface plasmons.

BACKGROUND ART

In recent years, in POCT (Point Of Care Testing), analysis chips (hereinafter refers to as "SPR chips") using SPR (Surface Plasmon Resonance) have been actively developed. The SPR chip includes a dielectric prism (dielectric medium) and a metal film which is formed over a surface of the dielectric prism and brought into contact with an observation sample.

When excitation light which advances through the inside of the dielectric prism is incident on an interface between the metal film and the dielectric prism while satisfying the total reflection, an evanescent wave leaks out from the interface. Thereby, interference between surface plasmons of the metal film and the evanescent wave is occurred. Further, the surface plasmons and the evanescent wave resonate at an angle at which a resonance angle is set to the incident angle of the excitation light to the interface. Since the resonance angle depends on the dielectric constant of the analysis subject sample, analysis is carried out according to a shift amount of the resonance angle due to the presence/absence of the sample.

Further, as a technique which uses the surface plasmon resonance, SPFS (Surface Plasmon-field enhanced Fluorescence Spectroscopy) is known other than the above-mentioned technique. An analysis chip (hereinafter refers to as "SPFS chips") using the SPFS is similar to the above-mentioned SPR chip in configuration for exciting the surface plasmons. The SPFS chip differs from the SPR chip in that the former provides an electric field enhancing effect of the evanescent wave caused when the surface plasmons and the evanescent wave resonate, and a florescent substance to the observation sample. In the detection, the above-mentioned enhanced electric field enhances fluorescence from the florescent substance provided to the sample, and by detecting the change, the SPFS chip can realize detection with high sensitively even using the sample having poor concentration, compared to the case using the SPR chip.

As for the analysis chips used in analysis with the above-mentioned surface plasmon resonance, for both the SPR chips and the SPFS chips, it is common in that the dielectric prism provided with the metal film is used as a part of the analysis chip and a specific linearly polarized light (P polarized light) is incident on the dielectric prism as the excitation light to generate the surface plasmon resonance. Further, in recent years, the analysis chips are preferably disposable for every measurement in consideration of efficiency, safety, and the like, of the measurement work, therefore, a dielectric prism materials has been changed from glass to resin which can be used at low cost.

However, by producing the dielectric prism with the resin, heat generated when the prism is formed and internal strain due to stress cause a disorder in a polarization state of the excitation light incident on the prism. For that reason, there have been problems such that a surface plasmon resonance state is unlikely occurred and the detection precision is deteriorated. Especially in the analysis with the SPFS chip, high-sensitive detection can be available as described above. Therefore, higher measurement precision is required in the analysis with the SPFS chip than in the analysis with the SPR chip. That is, it is required a sufficiently high polarization state maintenance rate and a uniform polarization state distribution.

Thereupon, in the case that the dielectric prism is made of the resin, it has been purposed a technique such that, for example, a correcting unit which compensates (corrects) birefringence is provided at a side of a measuring apparatus for performing the SPFS measurement, and the birefringence is corrected by the correcting unit to prevent the disorder of the polarization state (see Patent Document 1 below).

PRIOR ART DOCUMENT

Patent Document

[Patent Document 1] Japanese Unexamined Patent Application Publication No. 2009-236709

SUMMARY OF THE INVENTION

Problems to be Solved by the Invention

However, when correcting the birefringence by the above mentioned correcting unit, the correcting unit to correct the birefringence is newly required, the cost is increased, and evaluation/determination time takes longer.

The inventors of the present invention have newly found that the measurement sensitivity and precision can be improved by maintaining the polarization state of the incident excitation light at a high level, and by making the distribution of the polarization state uniform.

The present invention is therefore intended to provide prisms and sensor chips which can be produced at low cost, improve the measurement sensitivity and precision, and have the high-level polarization maintenance rate and the uniform polarization state distribution.

Means of Solving the Problems

In order to solve at least one of above problem, a prism of one aspect of the invention is the prism of a dielectric medium used in analysis utilizing surface plasmons. The prism comprises an incident surface on which excitation light is incident from outside, a reflective surface at which the excitation light incident on the incident surface is reflected, an emission surface from which the excitation light reflected by the reflective surface is emitted; and an opposite surface which opposes the reflective surface. The opposite surface is a recessed sink-mark surface.

In order to solve at least one of above problem, a sensor chip of one aspect of the invention comprises the prism according to claims 1 to 11 and a flow passage forming body in which a flow passage is formed.

Effects of the Invention

As described above, the prism according to the present invention can reduce cost and improve the measurement sensitivity and precision.

BRIEF DESCRIPTION OF THE DRAWINGS

FIG. 20 is a table illustrating the presence/absence of the sink mark and the P-polarization maintenance rate distribution state, for the different ejection methods.

MODES FOR CARRYING OUT THE INVENTION

Figure 1:
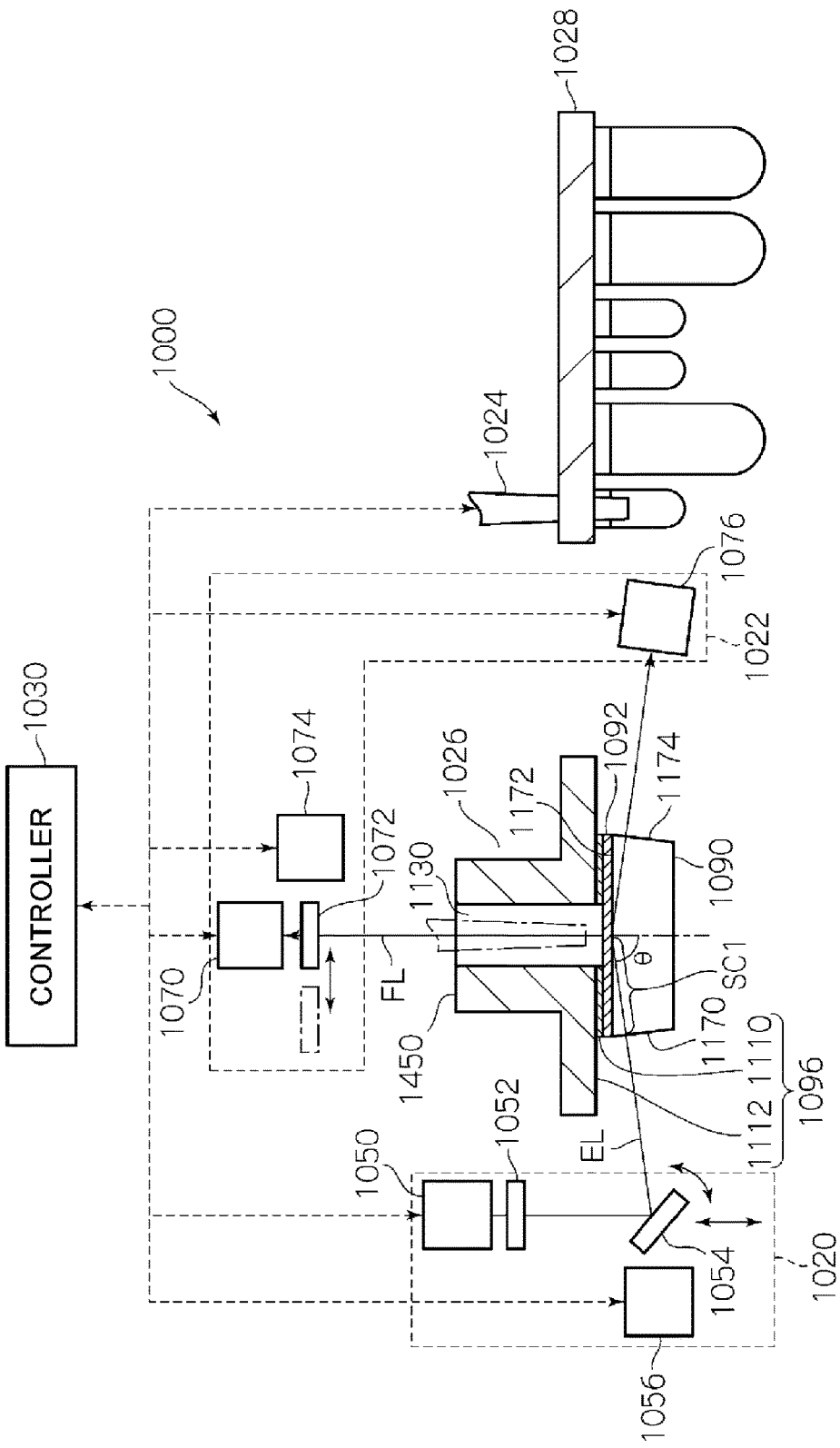
FIG. 1 is a schematic diagram of a measuring apparatus.

Hereinafter, the embodiment of the present invention is described with reference to the attached figures. Prior to describe the embodiment of a prism, an approximate configuration and each component of a measuring apparatus 1000 including the prism are firstly described. The measuring apparatus 1000 is an apparatus for performing measurement using the chip Surface Plasmon-field Fluorescence Spectroscopy (SPFS). FIG. 1 is a schematic view illustrating the whole configuration of the measuring apparatus.

Whole Configuration and Each Component of the Measuring Apparatus

As shown in FIG. 1, the measuring apparatus 1000 includes an irradiation mechanism 1020, a measurement mechanism 1022, a liquid feeding mechanism 1024, a sensor chip 1026, a reagent chip 1028, and a controller 1030. The irradiation mechanism 1020 includes a laser diode 1050, a linear polarizing plate 1052, a mirror 1054, and a mirror driving mechanism 1056. The measurement mechanism 1022 includes a photomultiplier tube 1070, a low-pass filter 1072, a low-pass filter driving mechanism 1074, and a photo diode 1076. Components other than the components mentioned-above may be added to the measuring apparatus 1000. Some of the components mentioned-above may be removed from the measuring apparatus 1000.

Sensor Chip

Figure 2:
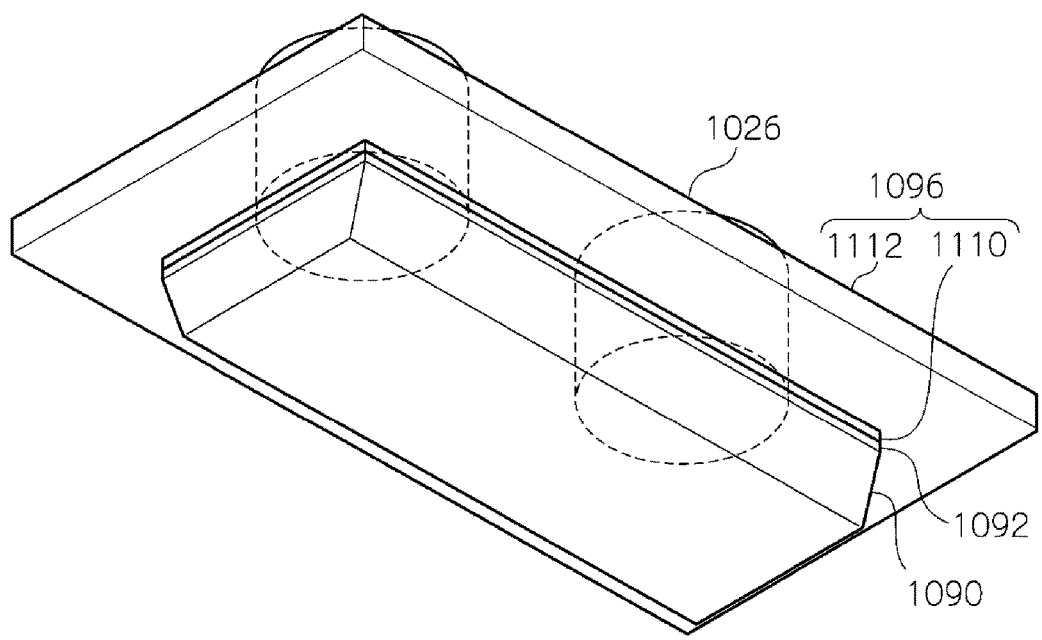
FIG. 2 is an outline perspective view of a sensor chip.

The sensor chip 1026 includes a prism 1090, a gold film 1092, and a flow passage forming body 1096, as shown in FIG. 2. The flow passage forming body 1096 includes a flow passage forming sheet 1110 and a flow passage forming top 1112. A not-shown flow passage is formed on the flow passage forming body 1096. The flow passage includes a supply route, a reaction chamber, and a collecting route. The reaction chamber is formed on the flow passage forming sheet 1110. The supply route and the collecting route are formed on the flow passage forming top 1112.

The sensor chip 1026 is sometimes called an "inspection chip", "analysis chip", "biochip", "sample cell", or the like. The sensor chip 1026 is a structure with the length of each side preferably being in a range from several millimeters to several centimeters, however, the chip 1026 may be replaced with a smaller-sized or a larger-sized structure which is far from being called as a "chip".

Prism

Figure 3:
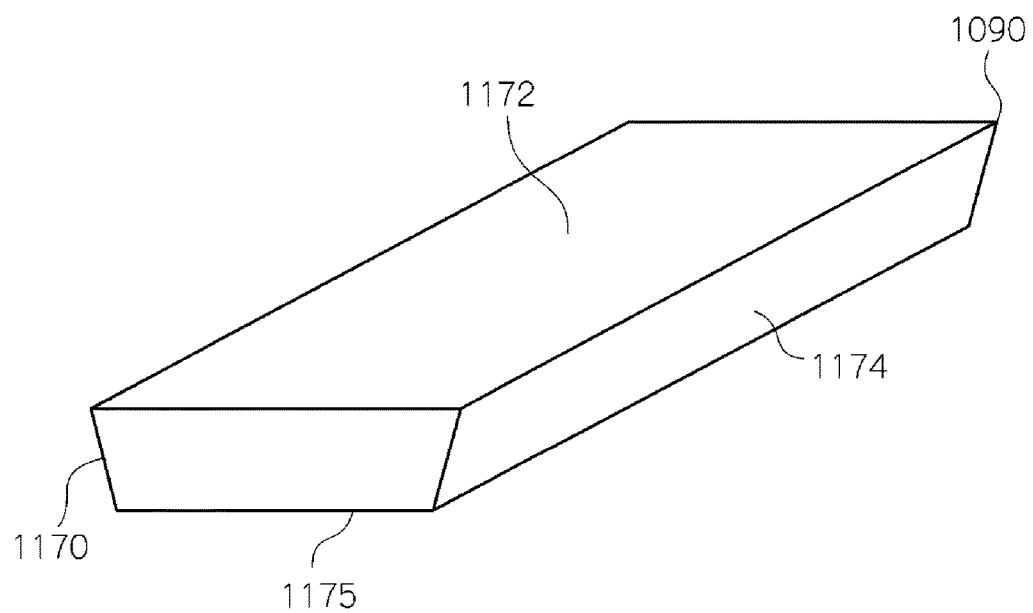
FIG. 3 is an outline perspective view of a prism.

The prism 1090 is, as shown in FIG. 3, a dielectric medium formed of resin which is transparent to excitation light EL, the shape thereof is a trapezoidal column body or preferably an isosceles trapezoidal column body. The shape of the prism 1090 is determined such that the excitation light EL can make incident on a reflective surface 1172 at an incident angle θ at which a degree of electrical field becomes maximum. The prism 1090 may be other than the trapezoidal column body, or may be replaced with an object which is far from being called as a "prism", as long as the above-mentioned requirements are met. For example, the prism may be a semicircular column body, or may be replaced with a plate. The production method for the prism 1090 will be described later.

The prism 1090 also includes, as shown in FIG. 3, an incident surface 1170, the reflective surface 1172, an emission surface 1174, and a sink-mark surface 1175. One of inclined side surfaces of the prism 1090 is the incident surface 1170, a wide parallel side surface of the prism 1090 is the reflective surface 1172, the other one of the inclined side surfaces of the prism 1090 is the emission surface 1174, and the opposite surface opposing the reflective surface 1172 is the sink-mark surface 1175.

Figure 4:
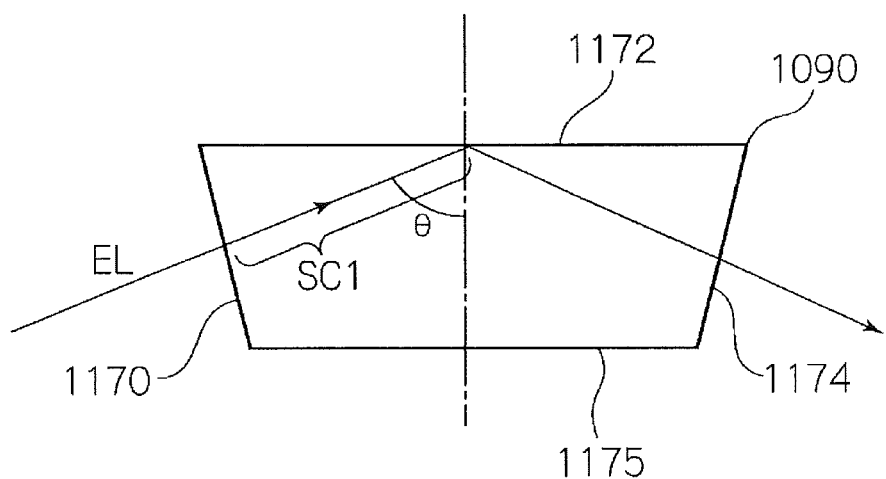
FIG. 4 is a longitudinal cross-sectional view of a prism.

In the prism 1090, as shown in FIG. 4, the incident surface 1170, the reflective surface 1172, and the emission surface 1174 are arranged so that the excitation light EL is incident on the incident surface 1170, reflected by the reflective surface 1172, and then emitted from the emission surface 1174.

Hereinafter, the resin material used for making the prism 1090 is described while referring to transparency, resistance to a liquid, hardness, water absorption, a reflective index, a photoelastic coefficient, autofluorescence, the relationship between a P-polarization component maintenance rate and SPR/SPFS measurement sensitivity, and the like.

Transparency

The material used for making the prism 1090 is transparent to the excitation light EL.

Resistance to a Liquid

The prism 1090 preferably has resistance against an organic solvent, an acidic solution, and an alkaline solution. The resistance is evaluated according to the test method specified by JIS K7114. The organic solvent is, for example, ethanol, isopropyl alcohol (IPA), acetone, N, N-dimethyl formamide (DMF), dimethyl sulfoxide (DMSO), or the like. The acidic solution is a solution having pH 4 to pH 7. The alkaline solution is a solution having pH 7 to pH 8.

Hardness of Prism

The hardness of the prism 1090 is preferably H or less. Thus, a mixed layer (conductor implanted layer) can be easily formed on the surface of the prism 1090, and adhesion strength between the conductor film and the prism is improved. The hardness is evaluated according to the test method specified by JIS K5401.

Water Absorption of Prism

The water absorption of the prism 1090 is preferably 0.2% or less, or more preferably 0.1% or less. Thus, the water absorbed by the prism 1090 is decreased when the prism 1090 is immersed in the liquid. The water absorption is evaluated according to the test method specified by JIS K7209. In JIS K7209, test methods regarding water absorption and boiling water absorption of plastic are specified.

Reflective Index of Prism

The reflective index (n) of the prism 1090 is 1.5 or more.

Prism Photoelastic Coefficient and P-Polarization Maintenance Rate

As the photoelastic coefficient of the prism 1090 is increased as the P-polarization component maintenance rate is decreased, therefore, the photoelastic coefficient of the resin material used for making the prism 1090 is preferably $80*10^{-12}$ $Pa^{-1}$ or less. Further, when a phase difference of a resin test piece of $\phi 11$, t=3 mm is evaluated according to the Senarmont method with light having a wavelength of 550 nm, the prism 1090 is produced using the resin material having the phase difference of the test piece in the gate vicinity of 153 nm or less, or more preferably 46 nm or less. Thus, even if the internal density of the prism 1090 becomes non-uniform, the light quantity of the P-polarization component incident on the reflective surface 1172 of the prism 1090 is increased. When the light quantity of the P-polarization component incident on the reflective surface 1172 of the prism 1090 is increased, the light quantity of surface plasmon excitation fluorescence FL is increased, and the measurement sensitivity and precision are improved.

Autofluorescence

In the SPFS analysis, when the sample quantity of the detection lower limit value is supplied, the light quantity of the autofluorescence emitted is less than the light quantity of the surface plasmon excitation fluorescence FL emitted from the sample. Here, the sample quantity is the antigen amount, and the concrete value of the antigen amount of the detection lower limit value is a small value, such as 0.25 mol, for example.

Prism Polarization Maintenance Rate and Polarization State Distribution

The P-polarization component maintenance rate of the P-polarization incident on the prism in the section from the incident surface to the reflective surface is 90% or more, or preferably 98%±2% in the detection range. Thus, the energy of the evanescent wave due to the surface plasmon resonance is transferred to the sample with the energy loss suppressed, and the SPR/SPFS measurement sensitivity and precision are improved.

P-Polarization Maintenance Rate Measuring Method

Figure 5:
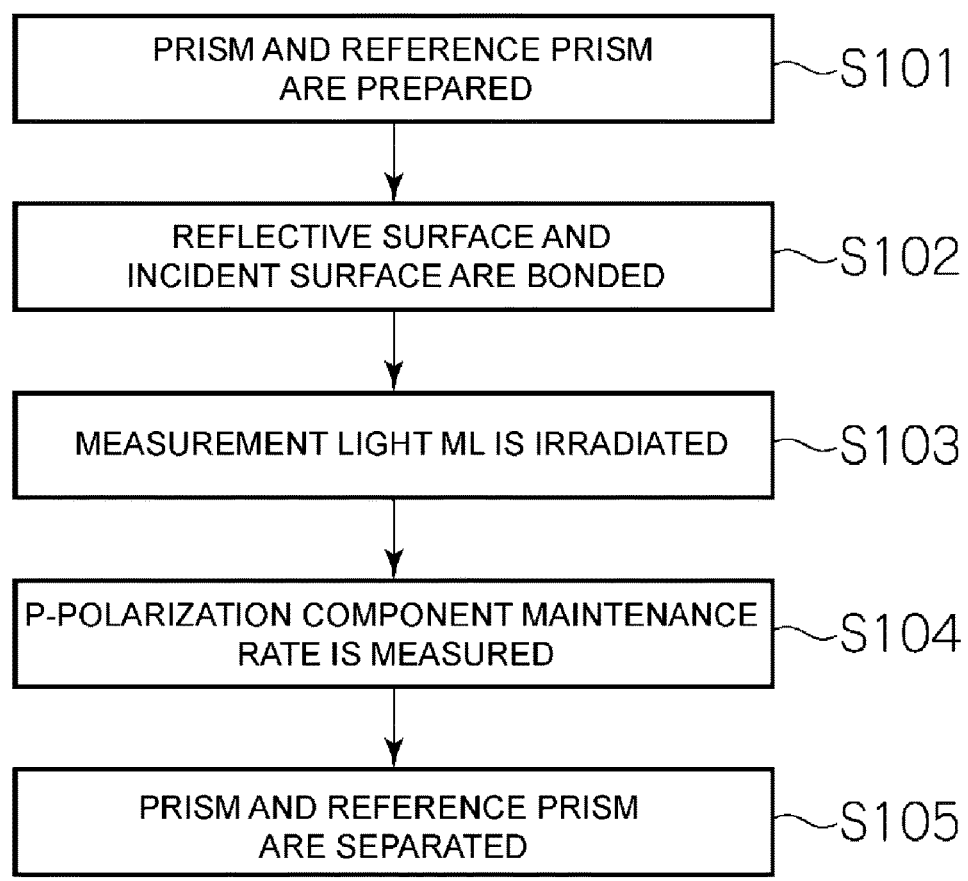
FIG. 5 is a flowchart illustrating maintenance rate measurement processes of a P-polarization component of a prism.

Here, the P-polarization maintenance rate measuring method is described with reference to FIG. 5. The flowchart in FIG. 5 illustrates measuring processes of the P-polarization component maintenance rate in the section from the incident surface to the reflective surface of the prism 1090. The schematic view in FIG. 6 illustrates the measuring apparatus for measuring the P-polarization component maintenance rate in the section from the incident surface to the reflective surface of the prism 1090.

Figure 6:
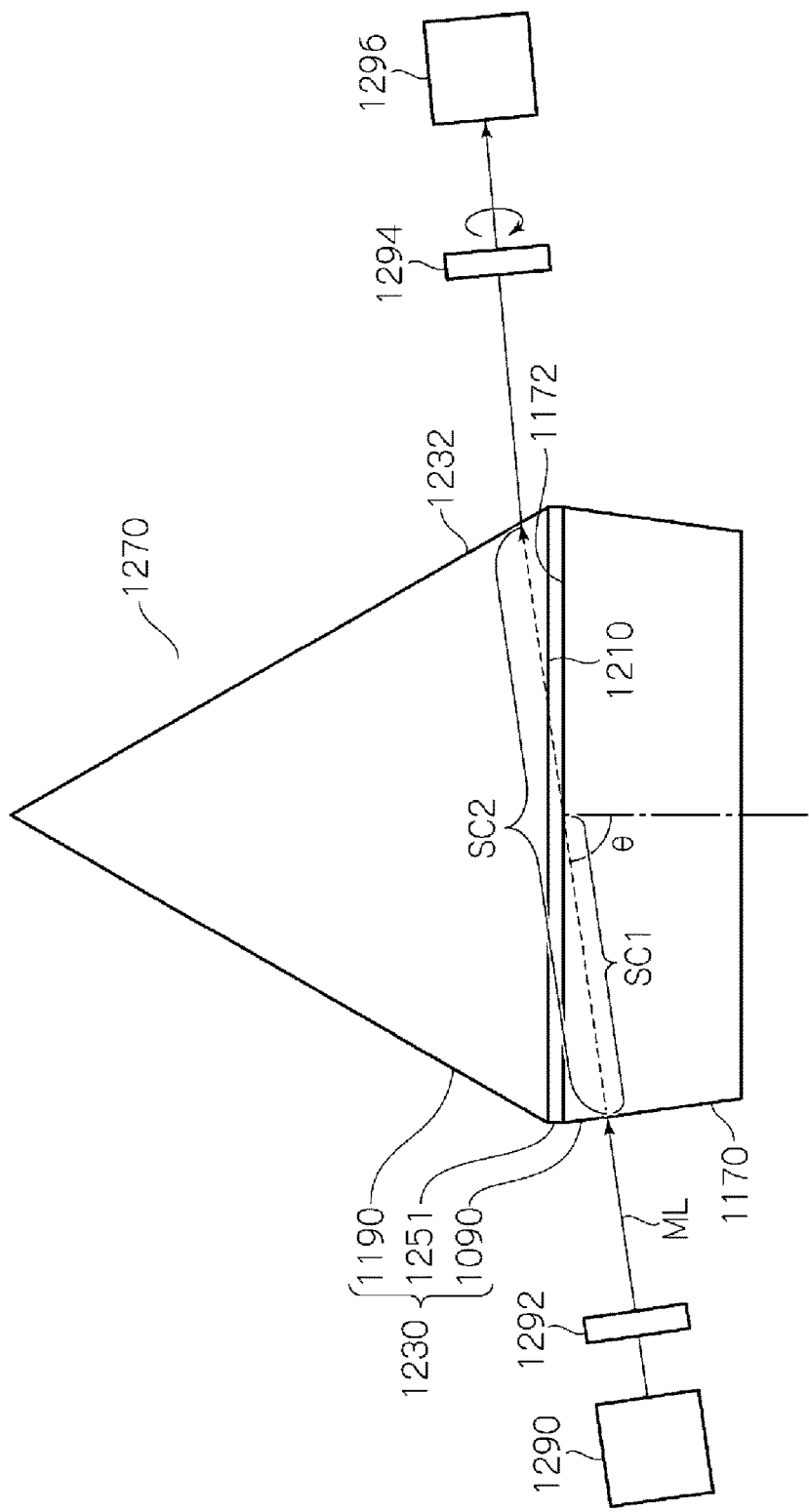
FIG. 6 is a dual view illustrating a measuring apparatus for a P-polarization component maintenance rate.

When the P-polarization component maintenance rate in a section SC1 is measured, the prism 1090 and a reference prism 1190 are prepared, as shown in FIG. 5 and FIG. 6 (step S101). The reference prism 1190 is made of a material which is transparent to the excitation light EL and causes no birefringence. The reference prism 1190 is, for example, made of glass, such as BK7, or the like. The refractive index of the prism 1090 and the refractive index of the reference prism 1190 are preferably allowed to coincide with each other. Thus, the refraction and the reflection of the light at the interface between the prism 1090 and the reference prism 1190 are suppressed, and the measurement of the P-polarization component maintenance rate in the section SC1 can be easily performed. However, even if the refractive index of the prism 1090 and the refractive index of the reference prism 1190 are not coincidence with each other, the measurement of the P-polarization component maintenance rate in the section SC1 can be performed.

After the prism 1090 and the reference prism 1190 are prepared, the reflective surface 1172 of the prism 1090 and an incident surface 1210 of the reference prism 1190 are bonded each other (step S102). Thus, a bonded body 1230 bonding the prism 1090 and the reference prism 1190 is produced. In the bonding, matching oil 1251 is preferably intervened between the reflective surface 1172 of the prism 1090 and the incident surface 1210 of the reference prism 1190. Thus, a space between the reflective surface 1172 of the prism 1090 and the incident surface 1210 of the reference prism 1190 becomes smaller, scattering of measurement light ML between the reflective surface 1172 of the prism 1090 and the incident surface 1210 of the reference prism 1190 is suppressed, and the P-polarization component maintenance rate in the section SC1 is easily measured. When the adhesion between the reflective surface 1172 of the prism 1090 and the incident surface 1210 of the reference prism 1190 is favorable, the matching oil 1251 may be omitted.

After the bonded body 1230 is produced, the bonded body 1230 is arranged to a measuring apparatus 1270 and the measurement light ML is irradiated to the bonded body 1230 (step S103). The measurement light ML is incident on the incident surface 1170 of the prism 1090, passed through the reflective surface 1172 of the prism and the incident surface 1210 of the reference prism 1190, and emitted from an emission surface 1232 of the reference prism 1190. The measurement light ML is irradiated from a laser diode 1290, passed through a polarizing rotator 1292, and incident on the incident surface 1170 of the prism 1090. The wavelength, the light quantity, the incident angle θ of the measurement light ML, are preferably allowed to coincide with the wavelength, the light quantity, and the incident angle θ of the excitation light EL, respectively. Thus, the P-polarization component maintenance rate in the section SC1 is measured under the condition same as the one when the light quantity of the surface plasmon excitation fluorescence FL is measured. The measurement light ML is linearly polarized light, and the polarized direction of the measurement light ML is adjusted in the polarized direction which is the same as that of the P polarized light with respect to the reflective surface 1172 of the prism 1090 by the fixed polarizing rotator 1292.

The laser diode 1290 is a He—Ne laser which emits light having a wavelength of 632 nm, for example, and emits a beam having a section diameter of 1 mm.

The P-polarization component maintenance rate is measured in a section SC2 from the incident surface 1170 of the prism 1090 to the emission surface 1232 of the reference prism 1190, while the measurement light ML is irradiated to the bonding body 1230.

Since the reference prism 1190 does not produce any birefringence, the P-polarization component maintenance rate in the section SC2 is considered as the same as the P-polarization component maintenance rate in the section SC1.

In the measuring apparatus 1270, the measurement light ML emitted from the emission surface 1232 of the reference prism 1190 passes through a polarizing rotator 1294 and reaches a power mater 1296. The polarizing rotator 1294 is made to rotate about an optical axis by angles up to 180° in units of 15°, and the light quantity of the measurement light ML is measured with the power meter 1296. Thus, the P-polarization component maintenance rate in the section SC1 is measured. The P-polarization component maintenance rate in the section SC1, however, may be measured by using other measuring methods.

After the P-polarization component maintenance rate in the section SC1 is measured (step S104), the prism 1090 and the reference prism 1190 are separated (step S105).

Autofluorescence Quantity Measurement

When the light quantity of the autofluorescence is measured, the Raman spectroscope is prepared and a fluorescence spectrum is measured. Laser light having a wavelength coincident with the wavelength of the excitation light EL is irradiated to the prism 1090. In the case that laser light having a wavelength of 632 nm is irradiated to the prism 1090, a filter for attenuating light having a wavelength of 650 nm or less is used when the autofluorescence light quantity is measured.

Specific Resin Example

The resin used for making the prism 1090 is preferably a cycloolffin polymer, or more preferably ZEONEX_E48R (trade name; hereinafter refers to as "E48R") manufactured by ZEON CORPORATION. The refraction rate of the E48R is 1.51 at a wavelength of 632 nm. The E48R has an advantage such that the autofluorescence light quantity emitted therefrom is small.

Figure 7:
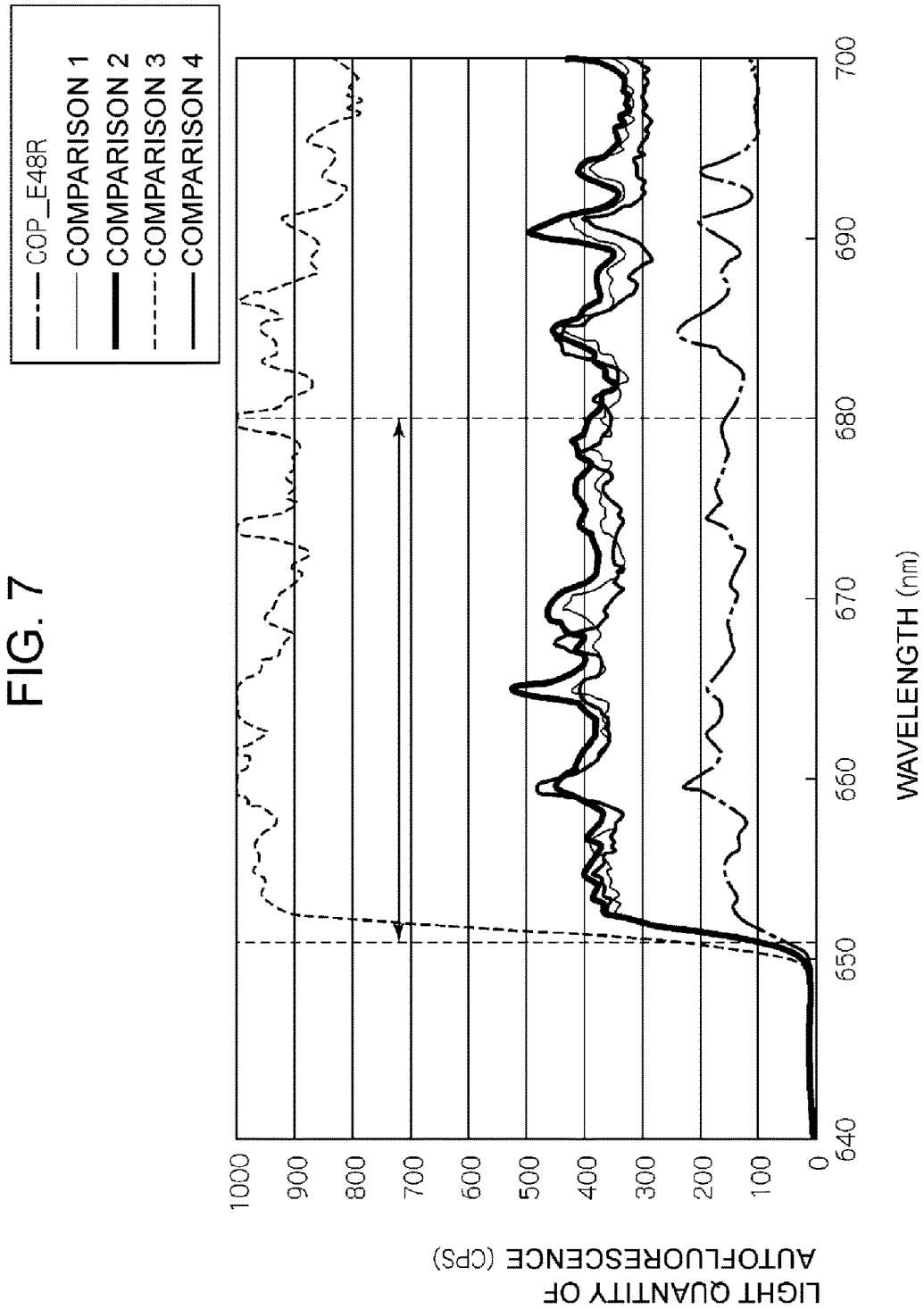
FIG. 7 is a graph illustrating autofluorescence spectral spectrums.

The graph in FIG. 7 illustrates autofluorescence spectral spectrums. In the FIG. 7, autofluorescence spectral spectrums of the E48R as well as "Comparison 1", "Comparison 2", "Comparison 3", and "Comparison 4" which are to be compared thereto are illustrated. In a wavelength range of 650 to 680 nm which is the measured wavelength range (detected light receiving range; a section shown by an arrow in FIG. 7) of the surface plasmon excitation fluorescence FL when the wavelength of the excitation light EL is 632 nm, the light quantity of the autofluorescence irradiated from the E48R is significantly smaller than that of the compared resin. Thus, the integrated intensity of the autofluorescence in the measured wavelength range in the E48R is also significantly small as shown in the Table below, is less than 5000 cps even taking a variation into consideration, and the light quantity of the autofluorescence is less than that of the surface plasmon excitation fluorescence FL.

Hardness of the Conductor Film Made of Gold Film

Figure 8:
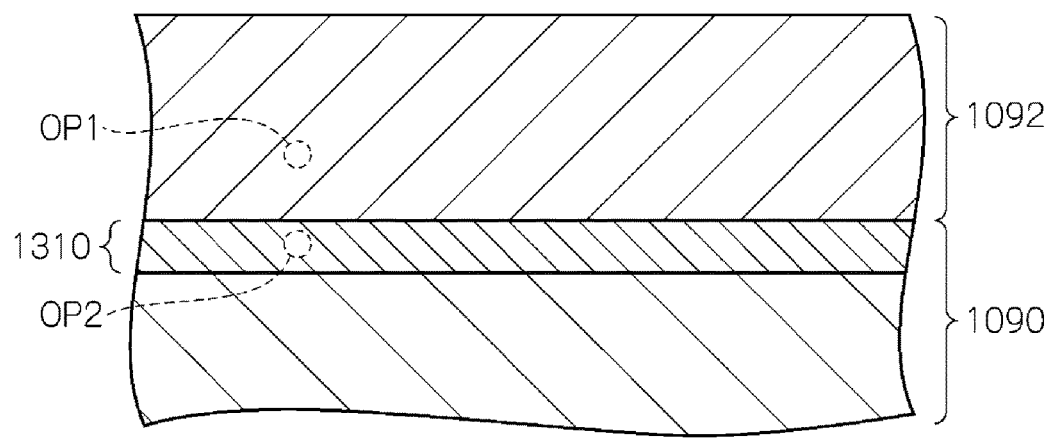
FIG. 8 is a cross-sectional view of the neighborhood of a border between a gold film and a prism.
Figure 9:
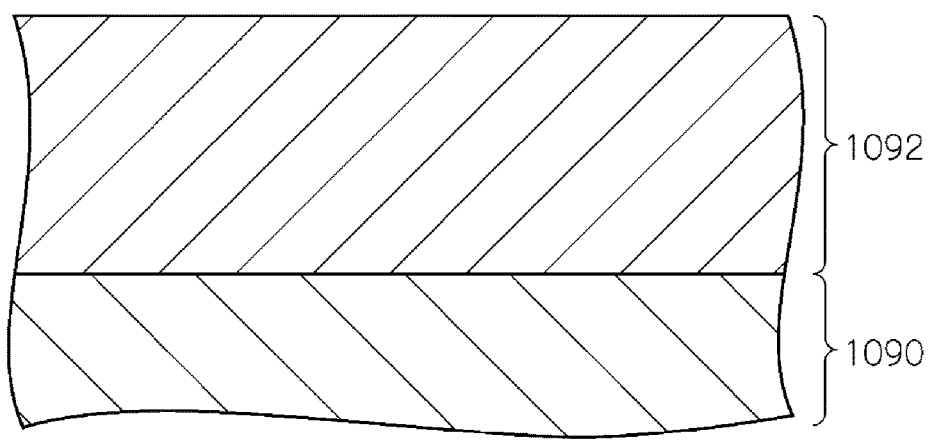
FIG. 9 is a cross-sectional view of the neighborhood of the border between the gold film and a prism.

In the case when a gold film having a film thickness of 40 nm to 50 nm is provided. The schematic views in FIG. 8 and FIG. 9 are cross-sectional views illustrating the neighborhood of a border between the gold film and the prism. FIG. 8 illustrates the case when the hardness of the prism is H or less. FIG. 9 illustrates the case when the hardness of the prism is larger than H. When the hardness is H or less, for example, ZEONEX_E48R (trade name) manufactured by ZEON CORPORATION (Chiyoda-ku, Tokyo) is used for making the prism 1090 and when the hardness of the prism 1090 is H, a mixed layer 1310 having a layer thickness of 2 to 3 nm is formed on the surface of the prism 1090, as shown in FIG. 8. When the cross-section is observed with the Focused Ion Beam-Transmission Electron Microscopy (FIB-TEM), it is observed that gold is included in not only an observation visual field OP1 on the cross-section of a gold film 1092 but also an observation visual field OP2 on the cross-section of the mixed layer 1310.

When the hardness is larger than H, for example, ZEONEX_330R (trade name) manufactured by ZEON CORPORATION is used for making the prism 1090 and the hardness of the prism 1090 is 3H, the mixed layer 1310 is not formed and sufficient film adhesiveness cannot be obtained.

Measurement

Before the measurement is performed with the measuring apparatus, an antigen is bound to an antibody fixed to a not-shown antigen capturing film (hereinafter refers to as a "fixed antibody") by immunoreactions (antigen-antibody reaction), and the antigen is captured by the antigen capturing film. The antibody which is subjected to fluorescence labeling (hereinafter refers to as a "fluorescence-labeled antibody") is then bound to the antigen by the immunoreactions, a fluorescence label is added to the antigen captured by the antigen capturing film.

When the measurement is performed, as shown in FIG. 1, the excitation light EL is irradiated by the irradiation mechanism 1020 to the prism 1090. The excitation light EL irradiated to the prism 1090 is advanced through the inside of the prism 1090 as shown in FIG. 4, reflected by the reflective surface 1172 (specifically, the interface between the prism 1090 and the gold film 1092), and emitted from the emission surface 1174. While the excitation light EL is being irradiated to the prism 1090, the evanescent wave leaks out from the interface between the prism 1090 and the gold film 1092 toward the gold film 1092 side, the electric field of the evanescent wave is enhanced by the resonance of the evanescent wave and the surface plasmons of the gold film. The incident angle θ of the excitation light EL incident on the interface between the prism 1090 and the gold film 1092 is selected so that the electric field enhancement of the evanescent wave is maximized. The enhanced electric field acts in the fluorescence label, and the surface plasmon excitation fluorescence FL is emitted from the antigen capturing film. The light quantity of the surface plasmon excitation fluorescence FL is measured by the photomultiplier tube 1070. The measurement result is transferred to the controller 1030, the interaction between the fixed antibody and the antigen is detected, and the presence/absence of the antigen, the antibody quantity, and the like, are then measured.

Liquid Feeding Mechanism

Back to FIG. 1, the liquid feeding mechanism 1024 supplies liquid, such as a sample liquid, a fluorescence label liquid, a buffer liquid, and the like, to the sensor chip 1026, and the liquid, such as the sample liquid, the fluorescence label liquid, the buffer liquid, and the like, is collected from the sensor chip 1026. When the liquid is supplied to the sensor chip 1026, each of the liquid is supplied to a supply port, the reaction chamber is filled with the liquid, and the liquid then reaches (contacts with) the antigen capturing film.

In the liquid feeding mechanism 1024, for example, the liquid is sucked from a liquid feeding source by a pump, the pump is transferred from the liquid feeding source to a liquid feeding destination, and the liquid is ejected to the liquid feeding destination by the pump. The liquid may be flowed through a piping connecting from the liquid feeding source to the liquid feeding destination.

Sample Liquid and Fluorescence Label Liquid

The sample liquid is typically objects, such as blood, and the like, extracted from human body, however, the sample liquid may be any object extracted from living creatures other than human being, and may also be any object extracted from non-living things. Preprocessing including dilution, blood cell separation, reagent mixing, and the like, may be performed onto the extracted objects.

The fluorescence label liquid includes a fluorescence label antigen which is bound to an antibody to be measured, and fluorescence-labeled. The fluorescence label antigen has a chemical structure to be a fluorescence label which emits fluorescence light.

Laser Diode

As shown in FIG. 1, the laser diode 1050 emits the excitation light EL. The laser diode 1050 may be replaced with a light source of other type. For example, the laser diode 1050 may be replaced with a light emitting diode, a mercury lamp, a laser other than a laser diode, or the like.

When the light emitted from the light source is not parallel rays, the light is converted to the parallel rays through a lens, a mirror, a slit, or the like. When the light is not linearly polarized light, the light is converted to the linearly polarized light through a linear polarizing plate, or the like. When the light is not monochromatic light, the light is converted to the monochromatic light through a diffraction grating, or the like.

Linear Polarizing Plate

As shown in FIG. 1, the linear polarizing plate 1052 is arranged on the optical path of the excitation light EL, and converts the excitation light EL emitted from the laser diode 1050 to linearly polarized light. The polarization direction of the excitation light EL is selected so that the excitation light EL becomes P polarized light with respect to the reflective surface 1172 of the prism 1090. Thus, the leakage of the evanescent wave is increased, the light quantity of the surface plasmon excitation fluorescence FL is increased, and the measurement sensitivity and precision are improved.

Mirror and Mirror Driving Mechanism

As shown in FIG. 1, the mirror 1054 is arranged on the optical path of the excitation light EL, and the excitation light EL reflected by the mirror 1054 which reflects the excitation light EL passes through the linear polarizing plate 1052 is irradiated to the prism 1090. The light irradiated to the prism 1090 is incident on the incident surface 1170, reflected by the reflected surface 1172, and emitted from the emission surface 1174. The incident angle θ of the excitation light EL against the reflective surface 1172 satisfies a total reflection condition $\theta_c \leq \theta$ ($\theta_c$: critical angle).

The mirror driving mechanism 1056 includes driving force sources, such as a motor, a piezoelectric actuator, and the like, rotates the mirror 1054, and adjusts the attitude of the mirror 1054. The mirror driving mechanism 1056 also comprises driving force sources, such as a linear stepping motor, and the like, causes the mirror 1054 to be transferred in the optical axis direction of the laser diode 1050, and adjusts the position of the mirror 1054. Thus, while maintaining the incident position of the excitation light EL at the reflective surface 1172 of the prism 1090 at the backside of a region where the antigen capturing film is fixed, an incident angle θ of the excitation light EL against the reflective surface 1172 of the prism 1090 can be adjusted.

Photomultiplier Tube

As shown in FIG. 1, the photomultiplier tube 1070 is arranged on the optical path of the surface plasmon excitation fluorescence FL, and measures the light quantity of the surface plasmon excitation fluorescence FL. The photomultiplier tube 1070 may be replaced with a light quantity sensor of other type. For example, the photomultiplier tube 1070 may be replaced with a charge coupled device (CCD) sensor, or the like.

Low-Pass Filter

The low-pass filter 1072 transmits light having a wavelength longer than a cutoff wavelength, and attenuates light having a wavelength shorter than the cutoff wavelength. The cutoff wavelength is selected from a range from the wavelength of the excitation light EL to the wavelength of the surface plasmon excitation fluorescence FL.

When the low-pass filter 1072 is arranged on the optical path of the surface plasmon excitation fluorescence FL, the scattered excitation light EL is attenuated by the low-pass filter 1072, and a small portion of the scattered excitation light EL reaches the photomultiplier tube 1070, however, the surface plasmon excitation fluorescence FL transmits the low-pass filter 1072, and a large portion of the surface plasmon excitation fluorescence FL reaches the photomultiplier tube 1070. Thus, when the light quantity of the surface plasmon excitation fluorescence FL having a relatively small light quantity is measured, the influence of the scattered excitation light EL having a relatively large light quantity is suppressed to improve the measurement precision. The low-pass filter 1072 may be replaced with a band-pass filter.

Low-Pass Filter Driving Mechanism

As shown in FIG. 1, the low-pass filter driving mechanism 1074 switches between the state that the low-pass filter 1072 is arranged on the optical path of the surface plasmon excitation fluorescence FL and the state that the low-pass filter 1072 is not arranged on the optical path of the surface plasmon excitation fluorescence FL.

Photo Diode

As shown in FIG. 1, the photo diode 1076 is arranged on the optical path of the excitation light EL reflected by the interface between the prism 1090 and the gold film 1092, and measures the light quantity of the excitation light EL reflected by the interface between the prism 1090 and the gold film 1092. The photo diode 1076 may be replaced with a light quantity sensor of other type. For example, the photo diode 1076 may be replaced with a photo transistor, a photo resister, or the like.

Controller

The controller 1030 is an incorporated computer for executing control programs. One incorporated computer may perform the function of the controller 1030, or two or more of incorporated computers may share to perform the functions of the controller 1030. Hardware without software may share to perform all or some of the functions of the controller 1030. The hardware is, for example, electrical circuits, such as an operational amplifier, a comparator, and the like. All or some of the processes performed by the controller 1030 may be executed manually, or outside of the measuring apparatus 1000.

Prism Production Method

Figure 10:
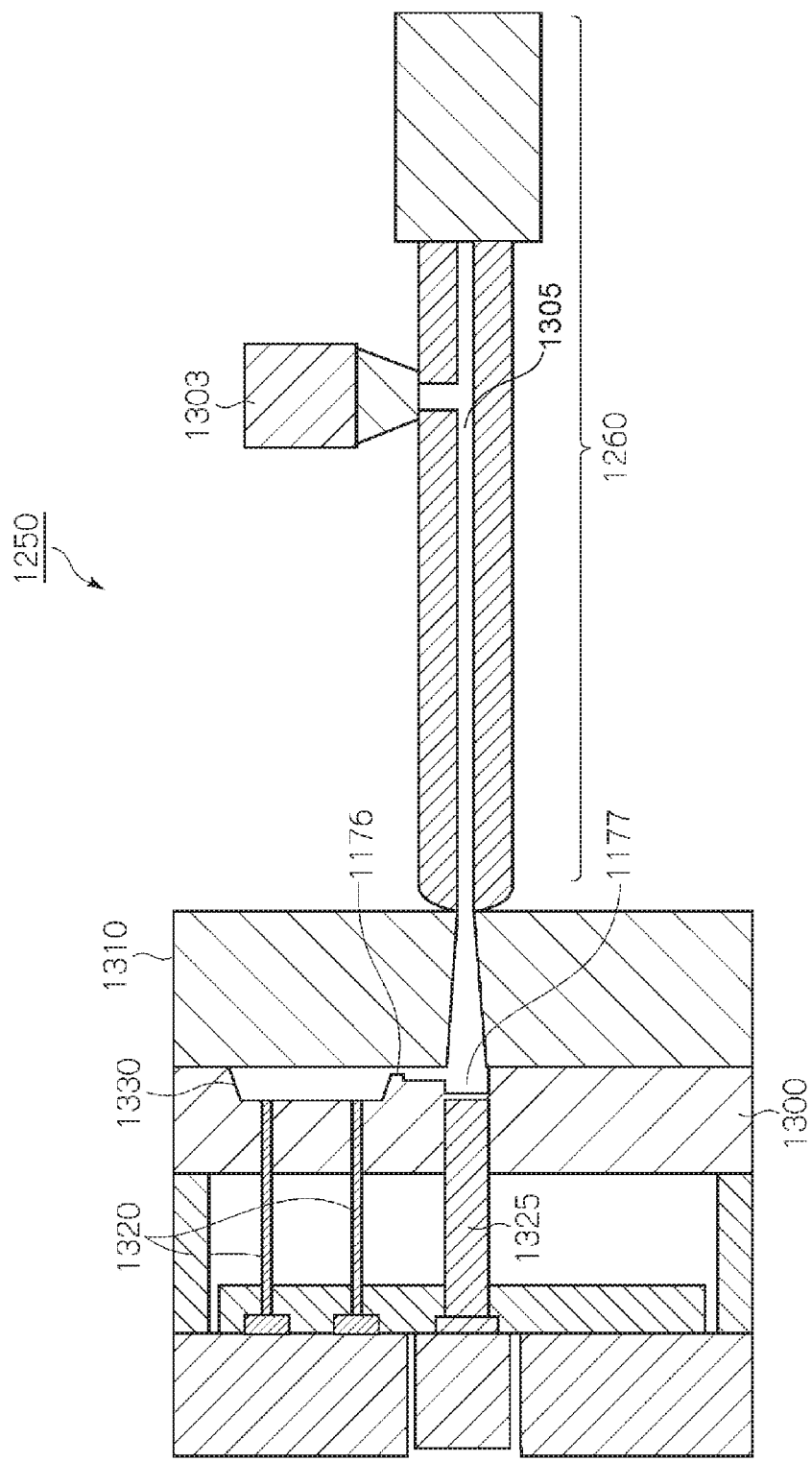
FIG. 10 is a schematic view illustrating the situation, in which a cavity is formed by making a movable mold and a fixed mold butt, so-called, a mold clamping process.
Figure 11:
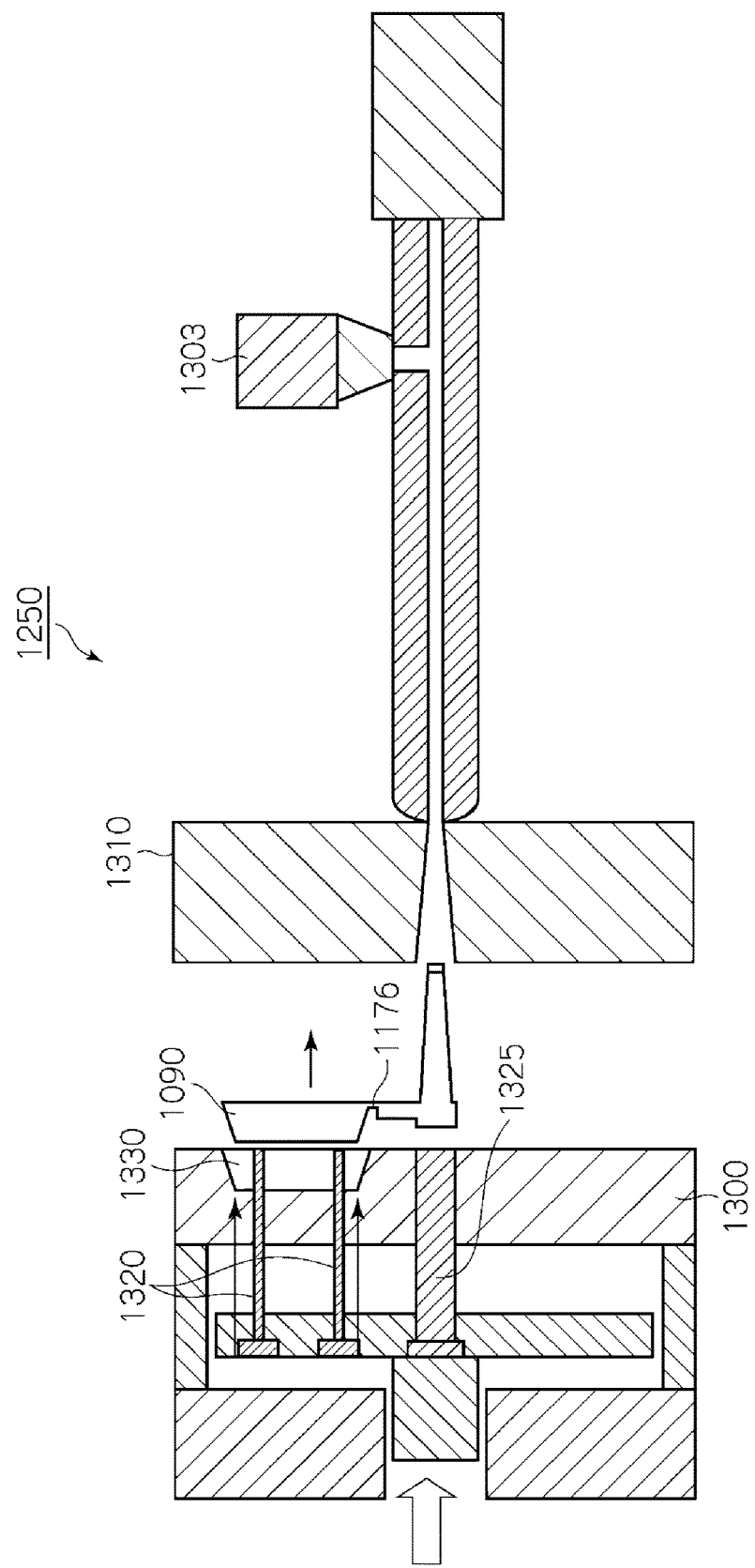
FIG. 11 is a schematic view illustrating the situation, in which a prism is released from an injection molding device, so-called, an ejection process.

The prism 1090 is completed through predetermined processes using an injection molding device. Here, injection molding processes using an injection mold is simply described with reference to FIG. 10 and FIG. 11. FIG. 10 is a schematic view illustrating the situation, in which a cavity is formed by making a movable mold and a fixed mold butt, so-called, a mold clamping process. FIG. 11 is a schematic view illustrating the situation, in which a prism is released from the mold, so-called, an ejection process.

As shown in FIG. 10, an injection mold 1250 include a movable mold 1300 in which a concave part (cavity) 1330 having an injection molding product shape is formed, a fixed mold 1310 having the function to close the concave part 1330 by butting to the movable mold 1300, ejecting pins 1320, an ejector member 1325, and a cylinder 1260 for supplying resin material of the material for the injection molding product to the cavity.

The injection molding processes include the mold clamping process, an injection process, a dwelling process, a cooling process, a mold opening process, and the ejection/product discharging process, and the injection molding is performed in this order. In the mold clamping process, as shown in FIG. 5, by making the movable mold 1300 and the fixed mold 1310 butt to close the concave part 1330 formed in the movable mold 1330, as a result, a cavity is formed. Resin material (molten resin) 1305 is then injected from a resin material supply furnace 1303, and the cavity s filled therewith (the injection process). The resin material is passed through a sprue 1177, and a gate 1176, and filled into the cavity. When the resin material is filled into the cavity of the mold, the resin material is cooled down in the mold and contracts. Since the resin volume is changed due to the contraction, the contractile function causes the dimensional change, poor shape-transcription, or the like, in the molding product. In order to prevent those failures, dwelling is performed at the molding device side for compensating the reduced portion of the resin due to the contraction (the dwelling process). The resin material is then cooled down in the mold to reach about a temperature at which the resin material can be taken out from the mold (the cooling process).

Next, the resin material 1305 is sufficiently cooled down after a predetermined time elapses, as shown in FIG. 11, the movable mold 1300 is released form the fixed mold 1310 (the mold opening process). At this time, the molding product is attached to the movable mold 1300. The prism 1090 is then released by causing the movable mold 1300 to slide the ejecting pins 1320 (the ejection process). The sensor chip 1026 is obtained by joining a not-shown substrate and a flow passage forming member to the prism 1090.

The sink mark occurred on a sink-mark surface 1175 of the prism 1090 is occurred during the above-mentioned dwelling process. The sink mark is occurred on the sink-mark surface 1175 at dwelling setting of 65 MPa or less. Further, ejection pin traces remain on an injection molding product in general during the ejection process, however, this time, ejection pin traces 1180 corresponding to the arrangement of the ejection pins 1320 are formed on the sink-mark surface 1175 of the prism 1090.

Relationship Between Sink Mark and Polarization Maintenance Rate

Internal stress of the prism 1090 of the molding product is increased by performing the dwelling, and the maintenance rate of the polarization state in the prism 1090 is deteriorated due to the internal stress. It has been found that, by lowering the dwelling setting so that the sink mark is occurred on the prism 1090, the internal stress applied to the prism 1090 is relaxed, and the polarization maintenance rate of the prism 1090 can be improved.

Relationship Between Gate Position and Sink Mark

The gate 1176 becomes an entrance port when the resin material is poured to the mold, and has a function to serve as an intermediary (interface) which fills the flowing resin material into the cavity via the sprue 1177. A gate width GW is 40% or less of a short-side length of the reflective surface 1172, and a gate thickness t2 is ½ or less of a prism thickness t1 (see FIG. 12A)

The prism 1090 is formed so that the position of the gate 1176 (gate position) is between a center C of the prism 1090 and the reflective surface 1172 in the thickness direction of the prism 1090. That is, according to the example in FIG. 12A, the gate 1176 is required to be formed at a position within a gate position range W.

Figure 12A:
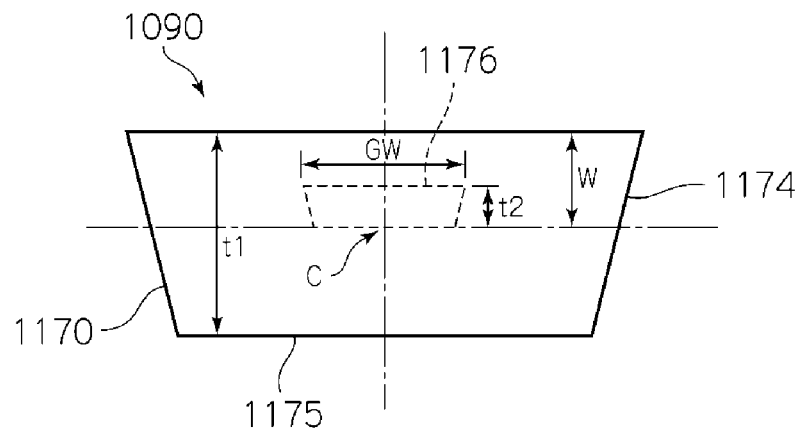
FIG. 12A is a view illustrating an example of the relationship between a gate position and a sink mark.
Figure 12B:
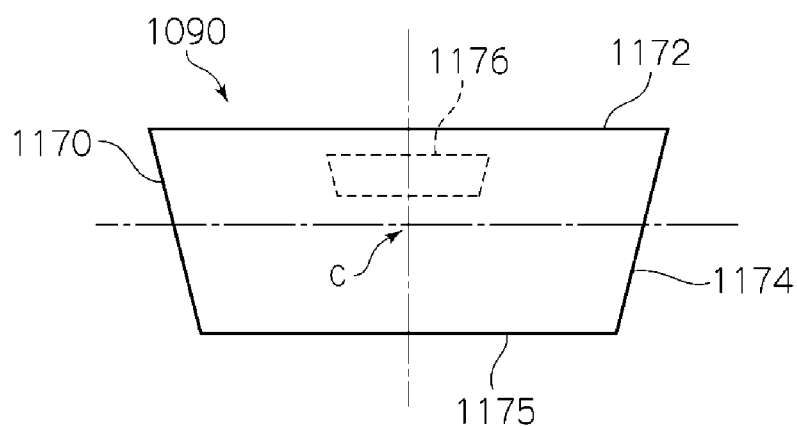
FIG. 12B is a view illustrating another example of the relationship between the gate position and the sink mark.
Figure 12C:
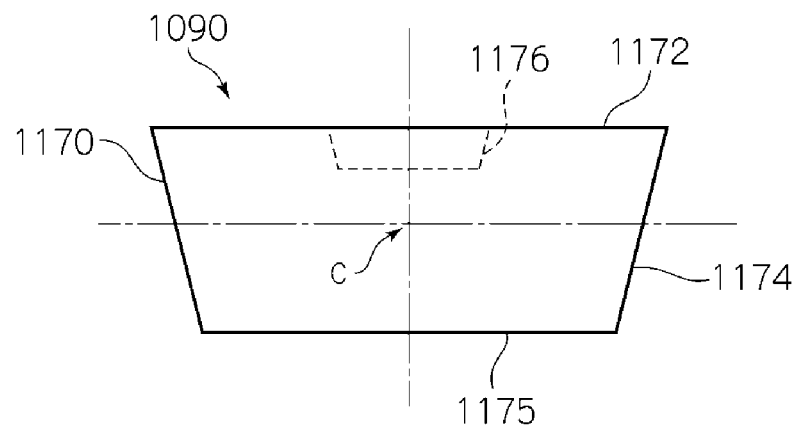
FIG. 12C is a view illustrating another example of the relationship between the gate position and the sink mark.

Gate arrangement which satisfies the above described conditions in FIG. 12A to FIG. 12C, that is, within the gate position range (within the W), is illustrated. As an example 1, as shown in FIG. 12A, the gate 1176 is arranged at the center C side of the prism 1090 in the thickness direction of the prism 1090. As a second direction, as shown in FIG. 12B, the gate 1176 is arranged at the intermediate between the center C of the prism 1090 and the reflective surface 1172 in the thickness direction of the prism 1090. As an example 3, as shown in FIG. 12C, the gate 1176 is arranged on the reflective surface 1172 in the thickness direction of the prism 1090.

By forming the prism 1090 so that the gate is arranged as described above, in the volume balance of the prism 1090 seeing from the gate, when seeing from the gate, the volume at the sink-mark surface side is increased, and heat shrinkage is shifted to the sink-mark surface side, therefore, the sink mark can be preferentially occurred at the sink-mark surface 1175.

Positional Relationship Between Prism Shape and Ejection Pin

Figure 13A:
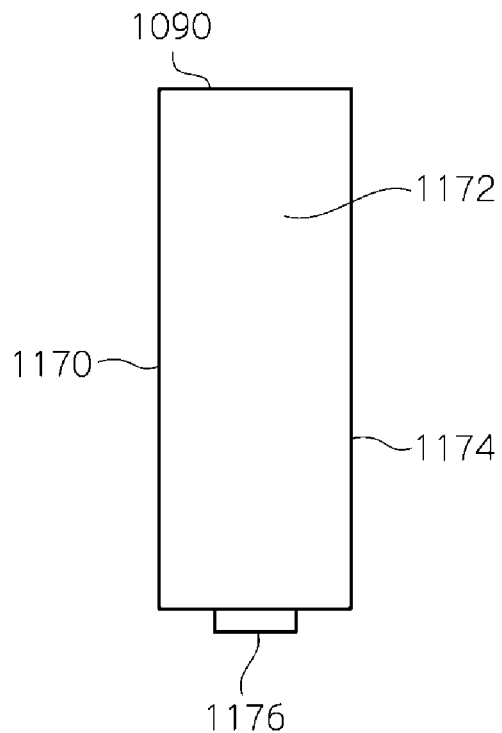
FIG. 13A is a plan view illustrating an example of the positional relationship between a prism shape and ejection pins.
Figure 13B:
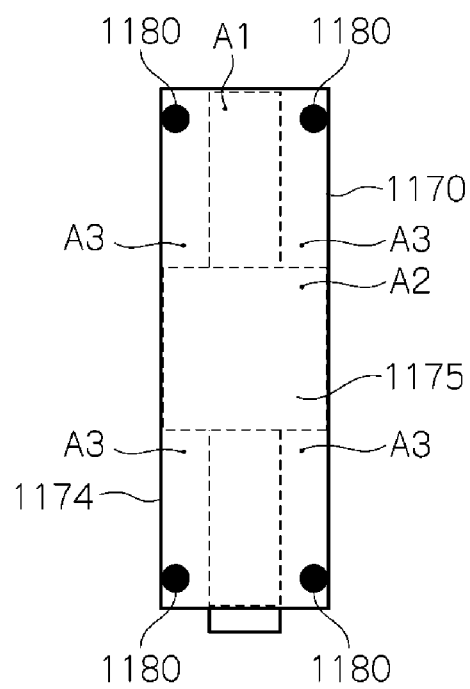
FIG. 13B is a bottom plan view of FIG. 13A.

Positional relationship between the shape of the prism 1090 and the traces 1180 of the ejection pins 1320 is required to satisfy the following conditions. Here, the traces 1180 of the ejection pins 1320 remain on the prism 1090 are at positions where the ejection pins 1320 are abutted on the prism 1090. As shown in FIG. 13B, the positions of the ejection pin traces 1180 are arranged in region A3 of the sink-mark surface 1175 other than a first projection region (hereinafter, refers to as a "gate extension region A1") obtained by projecting the gate extension region A1 obtained by extending the gate 1176 by the length of the prism 1090 in the longitudinal direction of the prism 1090 on the sink-mark surface 1175 and other than a second projection region (hereinafter, refers to as an "excitation light passing region A2") obtained by projecting the region where the excitation light EL passes through on the sink-mark surface 1175 (see FIG. 13B, FIG. 14B, and FIG. 15B). A plurality of the ejection pin 1320 may be provided in the region A3, and the shape and the material of the ejection pin 1320 are not limited. Here, the longitudinal direction of the prism 1090 is a direction orthogonal to the thickness direction and the width direction of the prism 1090.

As an example 1, as shown in FIG. 13B, the positions of the ejection pin traces 1180 are arranged somewhere other than the gate extension region A1 obtained by extending the gate 1176 by the length of the prism 1090 in the longitudinal direction of the prism 1090, and within the region A3 of the sink-mark surface 1175 other than the excitation light passing region A2. Further, one of the positions of the traces 1180 of the ejection pins 1320 is provided for each of the 4 corners (each region A3) of the sink-mark surface 1175.

Figure 14A:
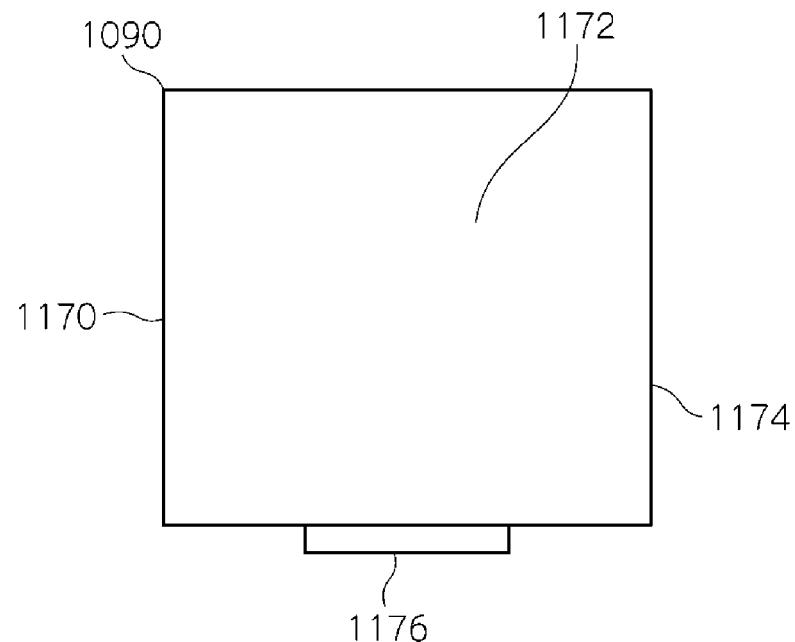
FIG. 14A is a plan view illustrating another example of the positional relationship between the prism shape and the ejection pins.
Figure 14B:
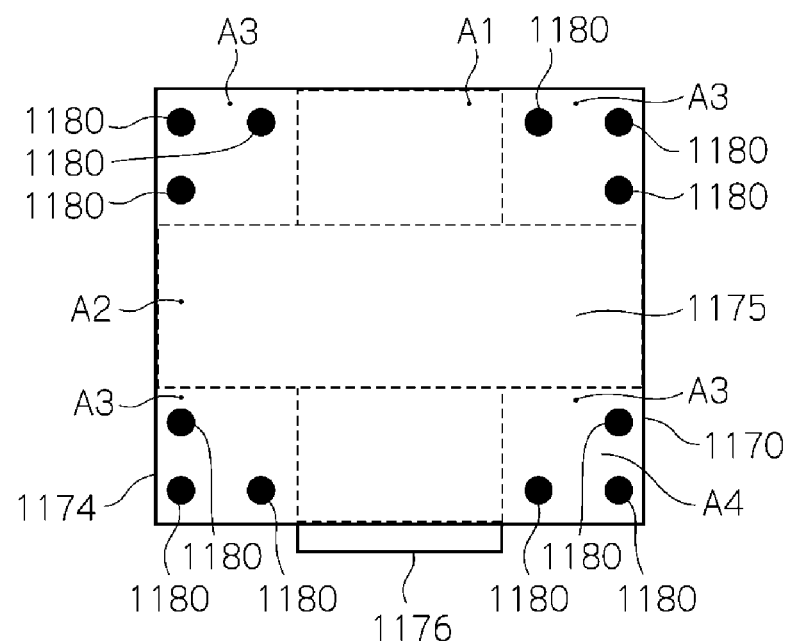
FIG. 14B is a bottom plan view of FIG. 14A.

As an example 2, as shown in FIG. 14B, the positions of the ejection pin traces 1180 are arranged somewhere other than the gate extension region A1 obtained by extending the gate 1176 by the length of the prism 1090 in the longitudinal direction of the prism 1090, and within the region A3 of the sink-mark surface 1175 other than the excitation light passing region A2. Further, three of the positions of the traces 1180 of the ejection pins 1320 are provided for each of the 4 corners of the sink-mark surface 1175.

Figure 15A:
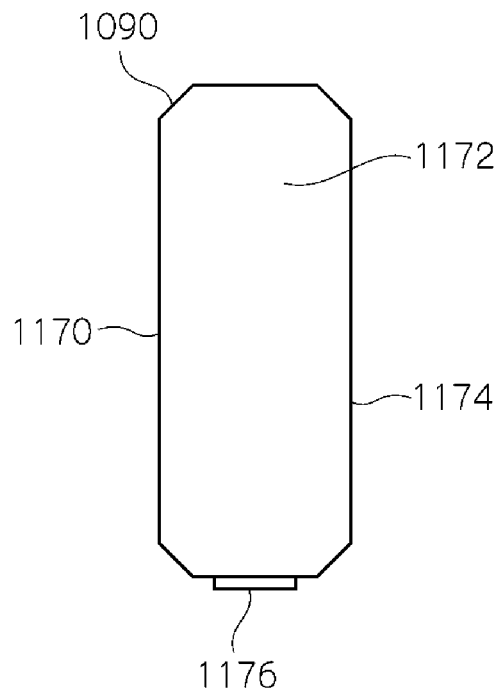
FIG. 15A is a plan view illustrating another example of the positional relationship between the prism shape and the ejection pins.
Figure 15B:
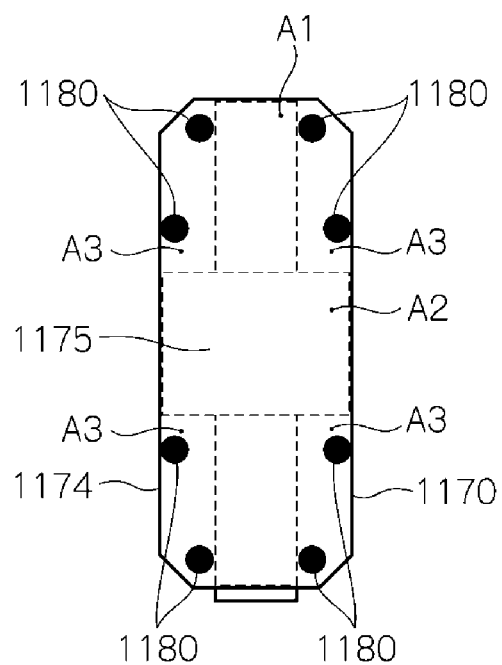
FIG. 15B is a bottom plan view of FIG. 15A.

As an example 3, as shown in FIG. 15B, the positions of the ejection pin traces 1180 are arranged somewhere other than the gate extension region A1 obtained by extending the gate 1176 by the length of the prism 1090 in the longitudinal direction of the prism 1090, and within the region A3 of the sink-mark surface 1175 other than the excitation light passing region A2. Further, two of the positions of the traces 1180 of the ejection pins 1320 are provided for each of the 4 corners of the sink-mark surface 1175.

Effects of forming the prism as described above will be described later.

Relationship Between Ejection Method and P-polarization Maintenance Rate

Figure 16A:
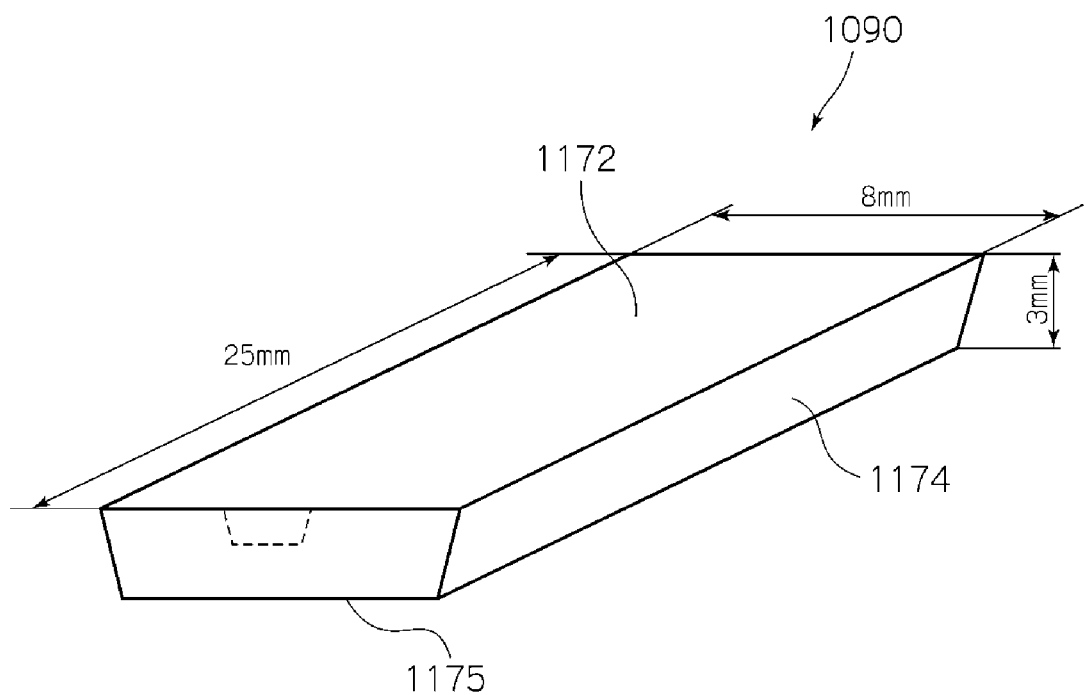
FIG. 16A is an outline perspective view of a prism used in measurement.
Figure 16B:
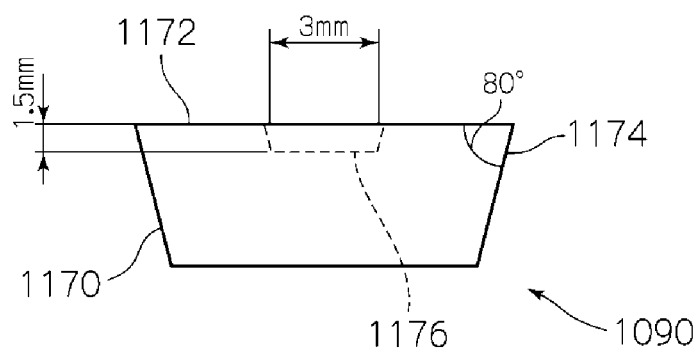
FIG. 16B is a longitudinal cross-sectional view of FIG. 16A.
Figure 19:
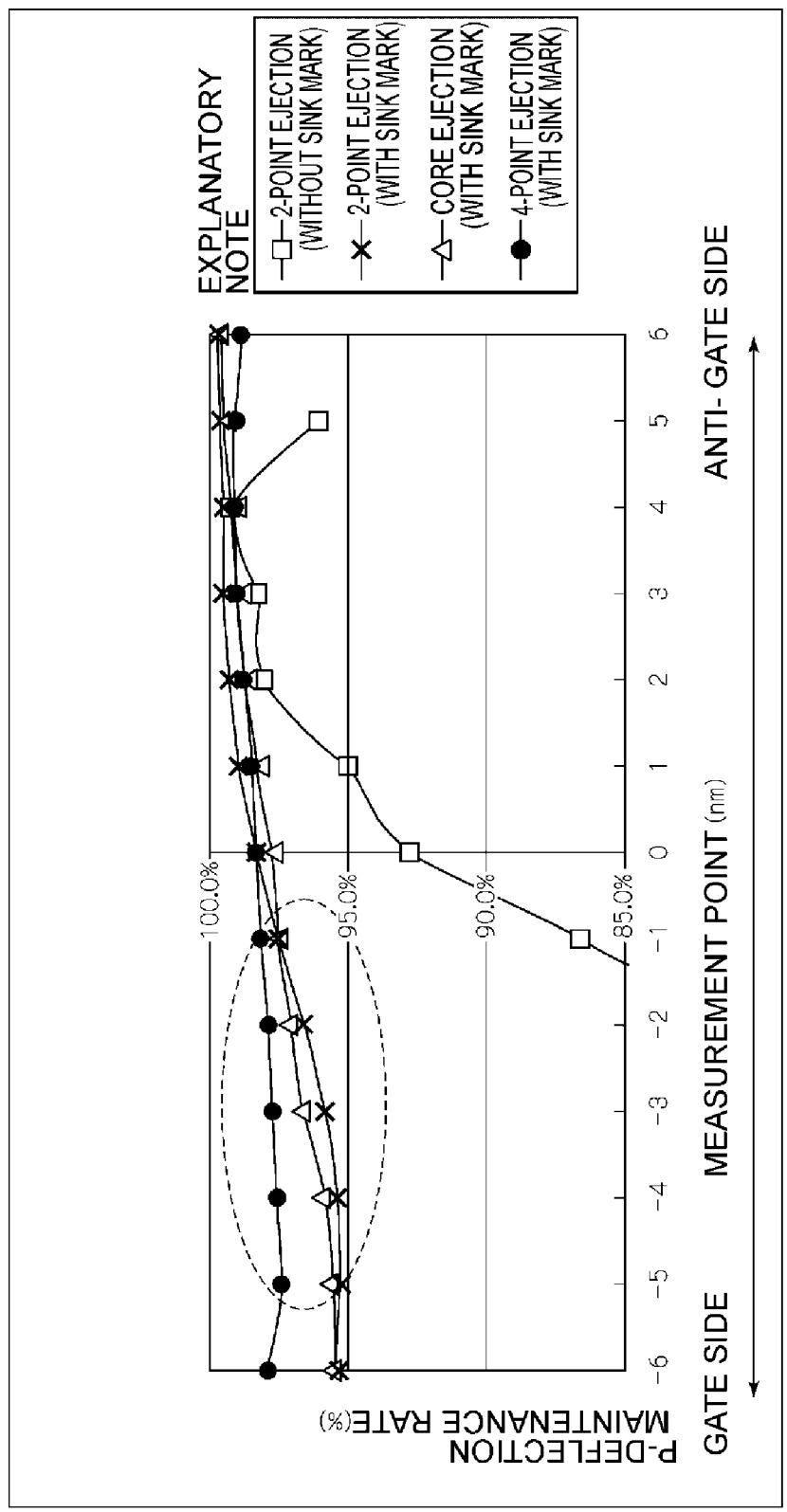
FIG. 19 is a graph illustrating a P-polarization maintenance rate distribution for presence/absence of a sink mark and different ejection methods.

Hereinafter, it is described the relationship between ejecting methods of the prism 1090, which is illustrated at the positions of the ejection pins 1320 and the ejection pin traces 1180, and the P-polarization maintenance rate distribution with reference to the presence/absence of the sink-mark surface 1175. In the present example, the trapezoidal prism 1090 shown in FIGS. 16A and 16B (a length of 25 mm, a width of 8 mm, a height of 3 mm, an inclination of trapezoidal side surface to the reflective surface of 80°, a gate width of 3 mm, and a gate thickness of 1.5 mm) is subjected to the measurement. The measurement method is to measure a P-polarization maintenance rate (%) in every ±1 mm from the center in the above mentioned detection range. FIG. 19 illustrates the measurement result. The birefringence distribution to the gate side is uniform (see the area surrounded by a broken line)

Figure 18A:
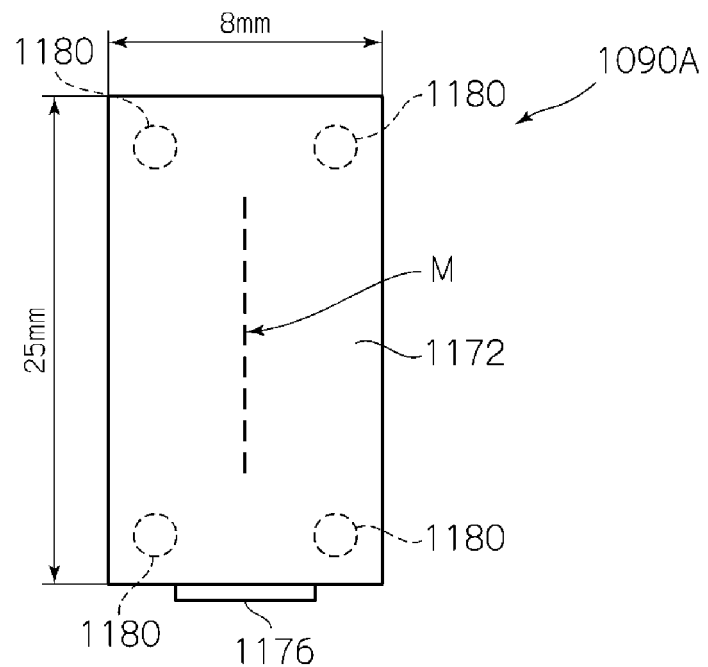
FIG. 18A is a plan view of a prism according to an example 3.
Figure 18B:
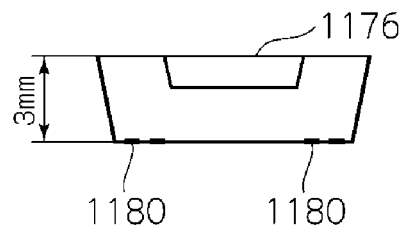
FIG. 18B is a longitudinal cross-sectional view of FIG. 18A.
Figure 18C:
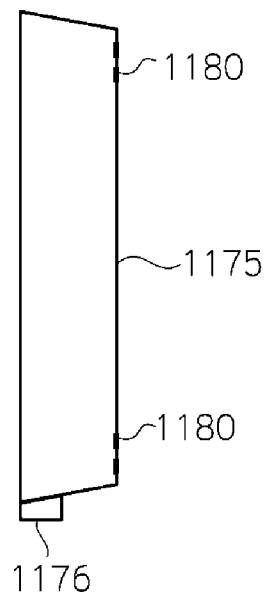
FIG. 18C is a side view of FIG. 18A.

The measurement subjects are a comparative example (2-point ejection without sink mark), an example 1 of the present invention (2-point ejection with sink mark), an example 2 (core ejection), and an example 3 (4-point ejection (4-corner ejection) with sink mark). As shown in FIG. 18A, a prism 1090A according to the example 3 is a prism in which the positions of the ejection pin traces 1180 are somewhere other than the gate extension range obtained by extending the gate 1176 by the length of the prism 1090 in the longitudinal direction of the prism 1090, and within the sink-mark surface 1175 region other than the excitation light passing region.

Figure 21A:
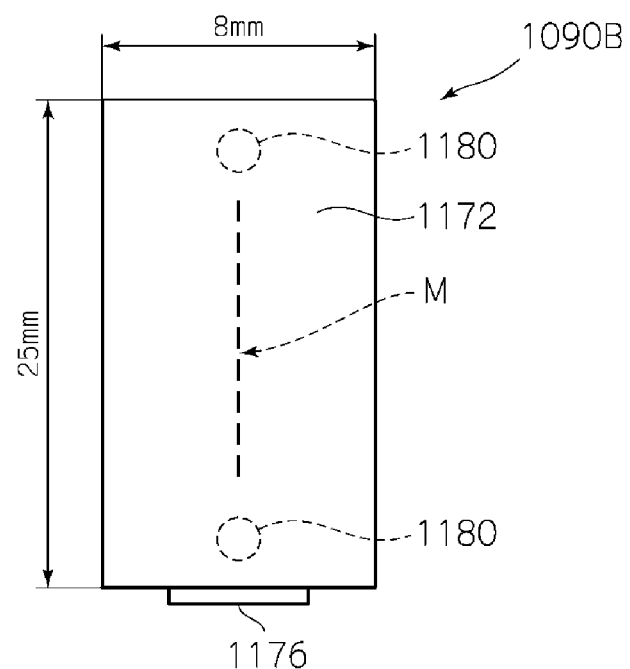
FIG. 21A is a plan view of a prism according to a comparative example and an example 1.
Figure 21B:
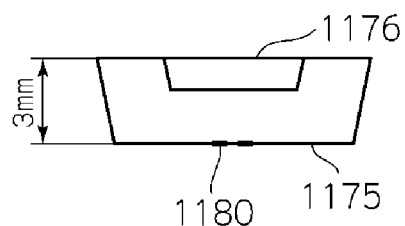
FIG. 21B is a longitudinal cross-sectional view of FIG. 21A.
Figure 21C:
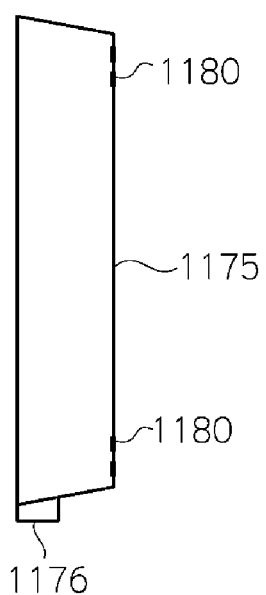
FIG. 21C is a side view of FIG. 21A.

A prism 1090B according to the comparative example is a prism, as shown in FIG. 21A, the position of ejection pin traces 1180 are arranged in the gate extension range obtained by extending the gate 1176 by the length of the prism 1090 in the longitudinal direction of the prism 1090, and within the sink-mark surface 1175 region other than the excitation light passing region, and has no sink mark on the sink-mark surface 1175.

Figure 22A:
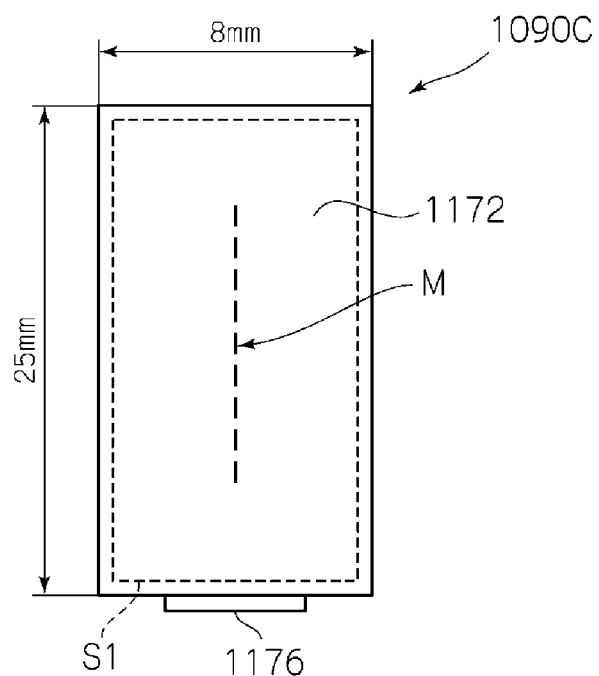
FIG. 22A is a plan view of a prism according to an example 2.
Figure 22B:
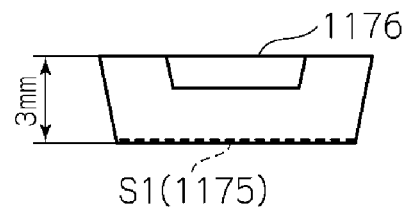
FIG. 22B is a longitudinal cross-sectional view of FIG. 22A.
Figure 22C:
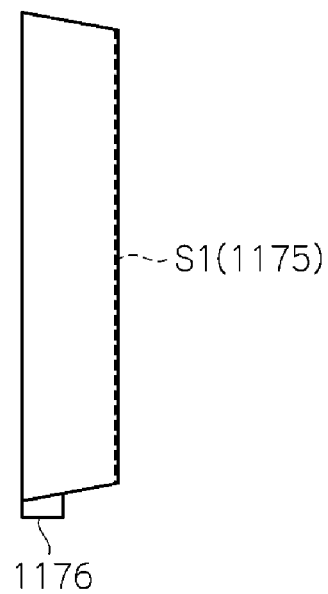
FIG. 22C is a side view of FIG. 22A.

The prism 1090B according to the example 1 is the same as that of the comparative example, except that the sink mark has been occurred in the sink-mark surface 1175. A prism 1090C according to the example 2 is, as shown in FIG. 22A, a prism formed with surface ejection (S1 in FIG. 22) by a not-shown core with the sink mark on the sink-mark surface 1175.

Figure 17A:
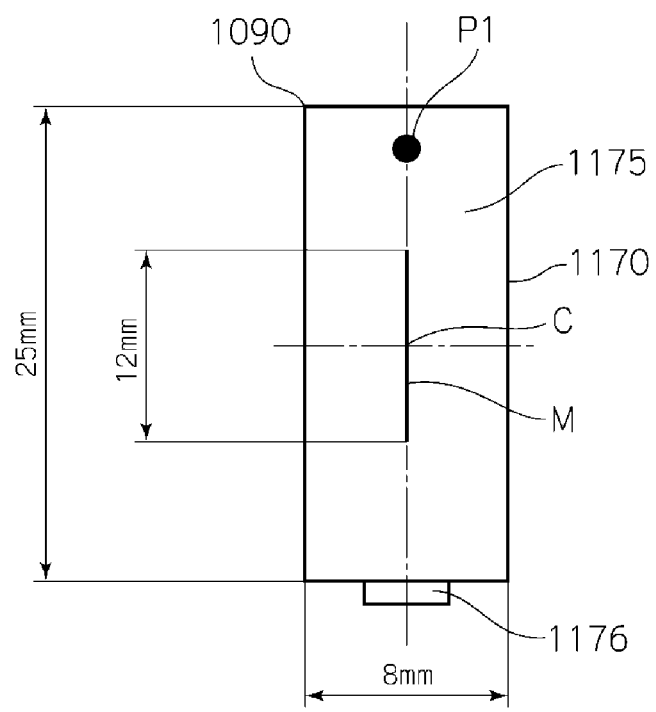
FIG. 17A is a plan view of a prism for describing sink mark amount measurement.
Figure 17B:
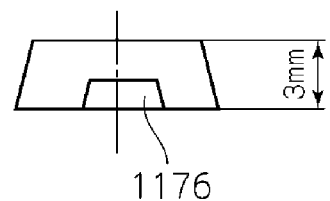
FIG. 17B is a longitudinal cross-sectional view of FIG. 17A.

Here, the measurement of a sink-mark amount is simply described with reference to FIGS. 17A and 17B. For the above described comparative example, the example 1, the example 2, and the example 3, the measurement results of the sink-mark amount occurred in the sink-mark surface 1175 are illustrated in FIG. 20. A height gauge is used for the measurement, and a height from a measurement reference point P1 (zero measurement height) is measured as sink-mark amount as illustrated in FIG. 17A. A measured range M is set as ±6 mm from the center C of the prism along the longitudinal direction thereof, as illustrated in FIG. 17A. The measured range M is set as ±6 mm in the present embodiment, however, it is not limited thereto.

The sink-mark amount (height) is 3 µm or less in the comparative example, the sink-mark amount (height) is 25 µm or more in the example 1, the sink-mark amount (height) is 25 µm or more in the example 2, and the sink-mark amount (height) is 25 µm or more in the example 3.

Further, the shapes and external dimensions of the prism and gate used are as mentioned above. "ZEONEX E48R (trade name)" is used as the resin material for the molding martial, and the prism is produced according to the above described "prism production method".

As described above, in the case that the P-polarization component maintenance rate (P-polarization maintenance rate) of the excitation light EL is 90% or more, or preferably 96% or more, and the maintenance rate distribution in a predetermined detection range (range of ±6 mm from the central position of the prism 1090 in the reflective surface region along the longitudinal direction of the prism in the present embodiment) is 95±5%, or more preferably 98±2%, it can be said that it is the distribution having a high polarization maintenance rate and a uniform polarization state, therefore, measurement sensitivity and precision can be improved.

From the measurement results taking the above described contents into consideration, in the example 1, the example 2, and the example 3, the P-polarization maintenance rate (%) is 90% or more over the whole range of the measurement. In the example 1, and the example 2, the P-polarization maintenance rate (%) is 95% or more over the whole range of the measurement. In the example 3, the P-polarization maintenance rate (%) is 96% or more over the whole range of the measurement, and the P-polarization maintenance rate distribution is 98±2%.

When an analysis in more detail is taken, in the comparative example, the P-polarization maintenance rate over the whole range of the measurement is not 90% or more, and the P-polarization maintenance rate distribution is not 98±2%.

In the example 1, the P-polarization maintenance rate is 90% or more over the whole range of the measurement, however, the P-polarization maintenance rate distribution is not 98%±2%, and the distribution is uniform from the point of view that whether the distribution is uniform or not, however, the range of the uniform distribution is narrower than that of the example 3.

In the example 2, the P-polarization maintenance rate is 90% or more over the whole range of the measurement, however, the P-polarization maintenance rate distribution is not 98%±2% like the example 1, and the distribution is uniform from the point of view that whether the distribution is uniform or not, however, the range of the uniform distribution is narrower than that of the example 3.

In the example 3, the distribution is uniform over the whole rage of the measurement.

Effects

As described above, it can be said that only the examples of the present invention provide a distribution having a high polarization maintenance rate and a uniform polarization state, therefore, it is possible to improve the measurement sensitivity and precision.

That is, according to the present invention, since even a resin dielectric prism can preferentially and stably generate a sink mark on a sink-mark surface of the prism and the sink-mark distribution can also be uniformed, therefore, a resin prism, having a high polarization maintenance rate and a uniform polarization state distribution, to be used for analysis using surface plasmon resonance can be provided at low cost.

A high-precision SPR/SPFS chip can be easily produced with low-cost, and a resin prism which is sufficiently usable for SPR/SPFS analysis can also be produced by using resin material having a photoelastic coefficient of $80*10^{-12}$ $Pa^{-1}$ or less or having a phase difference of 46 nm or more by Senarmont evaluation.

Figure 23:
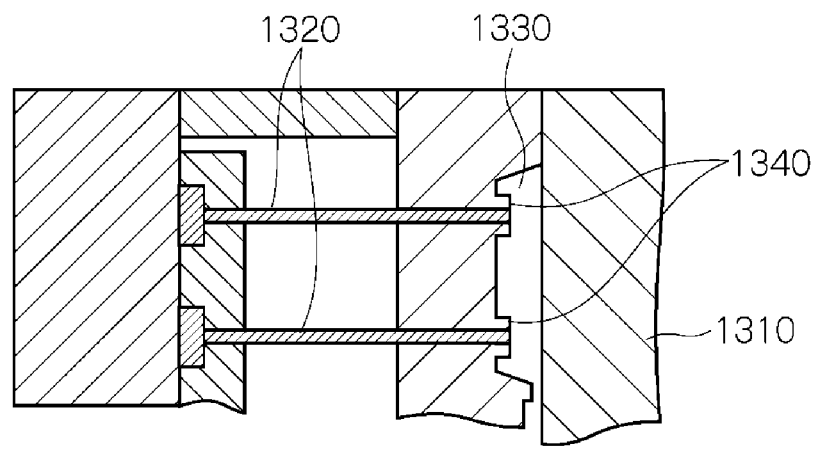
FIG. 23 is a schematic view when burr releasing parts are provided in FIG. 10.
Figure 24A:
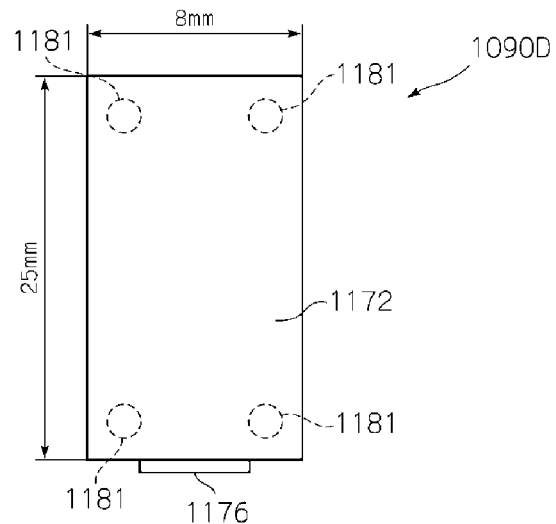
FIG. 24A is a plan view of a prism when the prism is injection-molded according to the mold schematic diagram in FIG. 23.
Figure 24B:
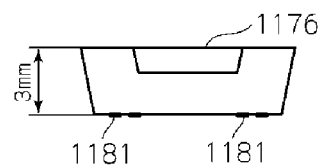
FIG. 24B is a longitudinal cross-sectional view of FIG. 24A.
Figure 24C:
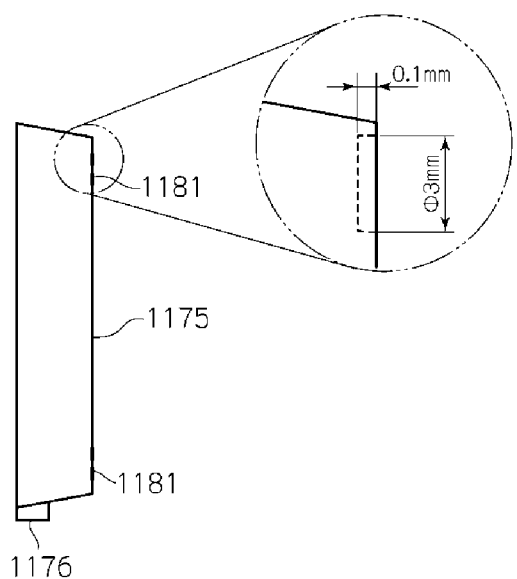
FIG. 24C is a side view of FIG. 24A.

In the ejection pin arrangement of the examples of the invention, it is described the case that no burr escape exists, however, a burr escape may be provided in the injection mold of 1340 in FIG. 23 for the case of avoiding the burr. FIGS. 24A, 24B, and 24C illustrate an example of a prism 1090D at 4-point (4-corner) ejection formed with the injection mold in FIG. 23. In FIGS. 24B and 24C, 1181 is made into the one to which the shape of a burr escape 1340 in FIG. 23 is transcripted onto the prism 1090D.

The present invention has been described in detail; however, the above descriptions are merely presented as examples in all aspects, and the invention is not limited thereto. Other various modified examples not exemplified above may be expected without departing from the scope of the invention.

The invention claimed is:
1. A prism of a dielectric medium used in analysis utilizing surface plasmons, comprising:

an incident surface on which excitation light is incident from outside;

a reflective surface at which the excitation light incident on the incident surface is reflected;

an emission surface from which the excitation light reflected by the reflective surface is emitted; and an opposite surface which opposes the reflective surface, wherein the opposite surface is a recessed sink-mark surface;

wherein an injection molding product formed such that the position of a gate, which becomes an entrance port when resin is poured into a mold, is between a center of the thickness direction and the reflective surface.

2. A sensor chip, comprising:
the prism according to claim 1; and
a flow passage forming body in which a flow passage is formed.

3. The prism according to claim 1, wherein a P-polarization component maintenance rate of the excitation light in a section from the incident surface to the reflective surface is 90% or more.

4. The prism according to claim 3, wherein
a distribution of the maintenance rate in a predetermined detection range is 95±5%.

5. A prism of a dielectric medium used in analysis utilizing surface plasmons, comprising:

an incident surface on which excitation light is incident from outside;

a reflective surface at which the excitation light incident on the incident surface is reflected;

an emission surface from which the excitation light reflected by the reflective surface is emitted; and an opposite surface which opposes the reflective surface, wherein the opposite surface is a recessed sink-mark surface;

wherein an injection molding product formed such that the position of a gate, which becomes an entrance port when resin is poured into a mold, is on an adjacent surface adjacent to each of the incident surface, the reflective surface, the emission surface, and the opposite surface, and the reflective surface and the opposite surface are approximately parallel, and the gate is provided closer to the reflective surface than the opposite surface.

6. The prism according to claim 5, wherein
a P-polarization component maintenance rate of the excitation light in a section from the incident surface to the reflective surface is 90% or more.

7. The prism according to claim 5, wherein
a distribution of the maintenance rate in a predetermined detection range is 95±5%.

8. A sensor chip, comprising:
the prism according to claim 5; and
a flow passage forming body in which a flow passage is formed.

9. A prism of a dielectric medium used in analysis utilizing surface plasmons, comprising:

an incident surface on which excitation light is incident from outside;

a reflective surface at which the excitation light incident on the incident surface is reflected;

an emission surface from which the excitation light reflected by the reflective surface is emitted; and an opposite surface which opposes the reflective surface, wherein the opposite surface is a recessed surface which curves towards an inside of the prism;

wherein a P-polarization component maintenance rate of the excitation light in a section from the incident surface to the reflective surface is 90% or more, the prism is formed of injection-molded resin; and the opposite surface curves towards the inside of the prism by an amount which is 25 µm or more and is smaller than a height of the prism.

10. The prism according to claim 9, wherein
a distribution of the maintenance rate in a predetermined detection range is 95±5%.

11. The prism according to claim 9, wherein
an injection molding product formed such that the position of a gate, which becomes an entrance port when resin is poured into a mold, is between a center of the thickness direction and the reflective surface.

12. A sensor chip, comprising:
the prism according to claim 9; and
a flow passage forming body in which a flow passage is formed.

* * * * *